US010028757B2

(12) United States Patent
Rolston

(10) Patent No.: US 10,028,757 B2
(45) Date of Patent: Jul. 24, 2018

(54) DISTAL FEMUR CUTTING BLOCK AND METHOD OF USING THE SAME

(71) Applicant: Zimmer, Inc., Warsaw, IN (US)

(72) Inventor: Lindsey R. Rolston, New Castle, IN (US)

(73) Assignee: Zimmer, Inc., Warsaw, IN (US)

( * ) Notice: Subject to any disclaimer, the term of this patent is extended or adjusted under 35 U.S.C. 154(b) by 537 days.

(21) Appl. No.: 14/423,901

(22) PCT Filed: Sep. 13, 2013

(86) PCT No.: PCT/US2013/059710
§ 371 (c)(1),
(2) Date: Feb. 25, 2015

(87) PCT Pub. No.: WO2014/043503
PCT Pub. Date: Mar. 20, 2014

(65) Prior Publication Data
US 2015/0190154 A1     Jul. 9, 2015

Related U.S. Application Data

(60) Provisional application No. 61/700,410, filed on Sep. 13, 2012.

(51) Int. Cl.
*A61B 17/15* (2006.01)
*A61B 17/17* (2006.01)
*A61F 2/46* (2006.01)

(52) U.S. Cl.
CPC ........ *A61B 17/1764* (2013.01); *A61B 17/155* (2013.01); *A61F 2002/4687* (2013.01)

(58) Field of Classification Search
CPC .................................................... A61B 17/155
(Continued)

(56) References Cited

U.S. PATENT DOCUMENTS

2004/0260301 A1   12/2004  Lionberger et al.
2007/0233141 A1*  10/2007  Park .................... A61B 17/155
                                                            606/88
(Continued)

FOREIGN PATENT DOCUMENTS

| EP | 2895089 | 7/2015 |
|---|---|---|
| WO | 2012024306 | 2/2012 |
| WO | WO-2014043503 A1 | 3/2014 |

OTHER PUBLICATIONS

"International Application Serial No. PCT/US2013/059710, International Search Report dated Dec. 31, 2013", 3 pgs.
(Continued)

*Primary Examiner* — David H Willse
(74) *Attorney, Agent, or Firm* — Schwegman Lundberg & Woessner, P.A.

(57) ABSTRACT

A distal femur cutting block comprising a first portion defining a first external surface, the first external surface including one or more first passages therethrough; and a second portion defining a second external surface, the second external surface including one or more second passages therethrough, the first portion hingedly connected to the second portion, wherein the first portion and the second portion may be rotated relative to each other through the hinged connection; and a third surface opposite one of the first surface or the second surface, the third surface comprising contours configured to substantially mate with at least one condyle of the distal femur.

17 Claims, 39 Drawing Sheets

(58) Field of Classification Search
USPC .......................................................... 606/88
See application file for complete search history.

(56) References Cited

U.S. PATENT DOCUMENTS

| | | |
|---|---|---|
| 2008/0161815 A1 | 7/2008 | Schoenefeld et al. |
| 2008/0195109 A1 | 8/2008 | Hunter et al. |
| 2009/0087276 A1* | 4/2009 | Rose .................. A61B 17/155 409/79 |
| 2009/0088763 A1 | 4/2009 | Aram et al. |
| 2010/0212138 A1 | 8/2010 | Carroll et al. |
| 2012/0116562 A1 | 5/2012 | Agnihotri et al. |

OTHER PUBLICATIONS

"International U.S. Appl. No. PCT/US2013/059710, International Preliminary Report on Patentability dated Mar. 26, 2015", 8 pgs.
"European Application Serial No. 13837725.4, Extended European Search Report dated Mar. 4, 2016", 7 pgs.
"European Application Serial No. 13837725.4, Communication Pursuant to Article 94(3) EPC dated Dec. 1, 2016", 5 pgs.
"European Application Serial No. 13837725.4, Response filed Apr. 10, 2017 to Communication Pursuant to Article 94(3) EPC dated Dec. 1, 2016", 13 pgs.

* cited by examiner

DISTAL FEMUR CUTTING BLOCK AND METHOD OF USING THE SAME

RELATED APPLICATION

This patent application is a U.S. National Stage Filing under 35 U.S.C. 371 from International Patent Application Serial No. PCT/US2013/059710, filed Sep. 13, 2013, published on Mar. 20, 2014 as WO 2014/043503 A1, which claims the benefit of priority to U.S. Provisional Patent Application No. 61/700,410, filed Sep. 13, 2012. The entire disclosures of which are hereby incorporated by reference in their entireties.

BACKGROUND

Within the last decade, orthopedic surgeons have successfully attached an implant to distal femurs to replace the medial joint and the patellofemoral joint. While such an implant has provided some patients with substantial relief from knee ailments, many patients have not benefited from the implant. There are several reasons why such implants are not effective with some patients. One reason is based on the sizing of the implant, particularly relating to the medial, lateral, and the AP dimensions of the implant. Currently, there are only a limited number of standard sizes of implants for use by surgeons. Because of the limited selection of implants, surgeons are often unable to provide patients with correctly sized implants. Another reason for ineffective implants is the inability of the implant to properly rotate. The implant must be able to properly rotate for proper patellar tracking and for balancing the knee through a full range of motion. Unfortunately, the placement of a femoral implant in the proper rotation can be difficult for surgeons to accomplish in a reproducible fashion. As a result, the risk of surgeon error in the placement of femoral implants is relatively high. A third reason for ineffective implants is the lack of instrumentation available to surgeons to make cuts to the distal femur in a reproducible fashion.

Accordingly, there exists a need for an apparatus and method of using the apparatus to prepare the distal femur for a joint replacement in a customizable manner such that all patients can benefit from the implant.

SUMMARY

The present disclosure includes disclosure of a distal femur cutting block and method of using the same. In at least one embodiment, such a distal femur cutting block comprises a first portion defining a first external surface, the first external surface including one or more first passages therethrough; and a second portion defining a second external surface, the second external surface including one or more second passages therethrough, the first portion hingedly connected to the second portion, wherein the first portion and the second portion may be rotated relative to each other through the hinged connection; and a third surface opposite one of the first surface or the second surface, the third surface comprising contours configured to substantially mate with at least one condyle of the distal femur. In an aspect of such an embodiment, at least one of the first passages comprises a cylindrical passage sized to receive a pin for fastening the first portion to the distal femur. In an aspect of such an embodiment, at least one of the second passages comprises a cylindrical passage sized to receive a drill for removing bone from the distal femur. In an aspect of such an embodiment, at least one of the second passages comprises a slot sized to receive an orthopedic bone saw blade for cutting the distal femur. In an aspect of such an embodiment, the second passages comprise slots for receiving one or more orthopedic bone saw blades, the slots being sufficient in number and arrangement to enable the distal femur in contact with the third portion to be shaped for receiving a femoral implant without removing the distal femur from the distal femur cutting block. In an aspect of such an embodiment, the first portion, the second portion, and the hinged connection are constructed from a single nylon article.

In at least one embodiment, such a distal femur cutting block comprises a first portion defining a first external surface, the first external surface containing one or more first passages therethrough, the first portion comprising a seam along a longitudinal axis thereof, the seam dividing the first portion into two substantially similar sections; a second portion defining a second external surface, the second external surface containing one or more second passages therethrough, the second portion being integral with and arranged at substantially a right angle to the first portion, the seam continuing into the second portion but not through the second external surface thereby forming a hinge at the second external surface; and a third surface opposite one of the first surface or the second surface, the third surface comprising contours configured to substantially mate with at least one condyle of the distal femur. In an aspect of such an embodiment, at least one of the first passages comprises a cylindrical passage sized to receive a pin for fastening the first portion to the distal femur. In an aspect of such an embodiment, at least one of the second passages comprises a cylindrical passage sized to receive a drill for removing bone from the distal femur. In an aspect of such an embodiment, at least one of the second passages comprises a slot sized to receive an orthopedic bone saw blade for cutting the distal femur. In an aspect of such an embodiment, the second passages comprise slots for receiving one or more orthopedic bone saw blades, the slots being sufficient in number and arrangement to enable the distal femur in contact with the third portion to be shaped for receiving a femoral implant without removing the distal femur from the distal femur cutting block. In an aspect of such an embodiment, the first portion and the second portion are constructed from a single nylon article.

In at least one embodiment, such a distal femur cutting block comprises a block having a first surface, the first surface comprising contours configured to substantially mate with at least one condyle of a distal femur, and a second surface opposing the first surface; and at least one passage through the block, the at least one passage configured to permit a medical instrument introduced into the passage at the first surface to emerge from the passage at the second surface, wherein when the second surface is adjacent the at least one condyle of the distal femur, the medical instrument is aligned by the passage into a position to contact the at least one condyle. In an aspect of such an embodiment, at least one of the passages comprises a cylindrical passage sized to receive a pin for fastening the first block to the distal femur. In an aspect of such an embodiment, at least one of the passages comprises a cylindrical passage sized to receive a drill for removing bone from the distal femur. In an aspect of such an embodiment, at least one of the passages comprises a slot sized to receive an orthopedic bone saw blade for cutting the distal femur. In an aspect of such an embodiment, the passages comprise slots for receiving one or more orthopedic bone saw blades, the slots being sufficient in number and arrangement to enable the distal femur in contact with the first surface to be shaped for receiving a femoral implant without removing the distal femur from the contact with the first surface. In an aspect of such an embodiment, the distal femur cutting block further comprises a seam along the first surface, the seam dividing the first surface into two substantially similar sections, the seam continuing into the block but not through the second surface thereby forming a hinge at the second external surface.

In at least one embodiment, such a method for utilizing a distal femur cutting block comprises the steps of receiving at least a portion of a distal femur in a distal femur cutting block; performing operations on the distal femur using guides on the distal femur cutting block; removing the distal femur cutting block from the distal femur; and applying an implant to the distal femur. In an aspect of such an embodiment, the distal femur cutting block comprises a flexible hinge, and the step of receiving at least a portion of a distal femur in a distal femur cutting block comprises the step of bending the distal femur cutting block at the flexible hinge.

BRIEF DESCRIPTION OF THE DRAWINGS

The features and advantages of this disclosure, and the manner of attaining them, will be more apparent and better understood by reference to the following descriptions of the disclosed methods and systems, taken in conjunction with the accompanying drawings, wherein.

DESCRIPTION

Figure 1:
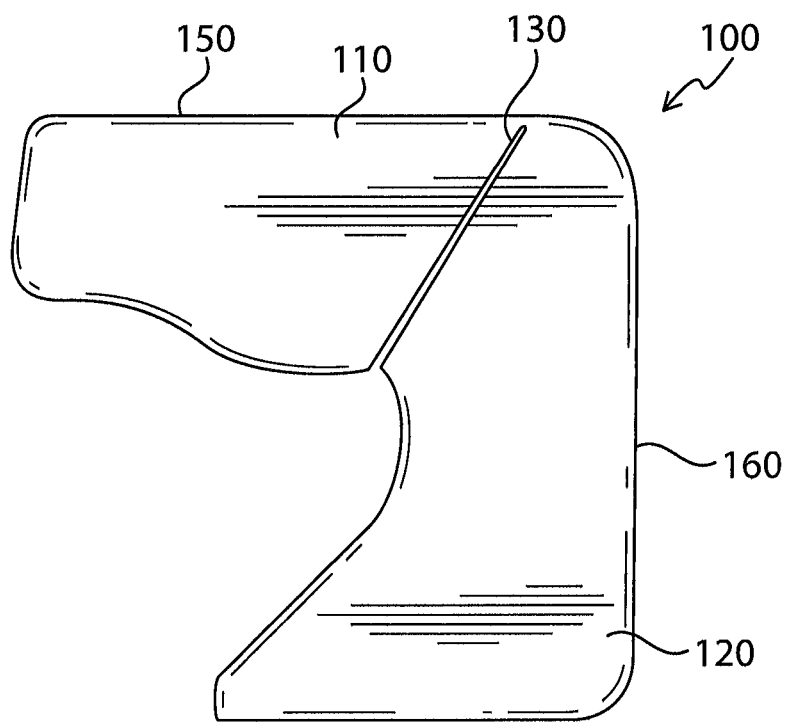
FIG. 1 shows a side view of a distal femur cutting block according to at least one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1 shows a distal femur cutting block 100 according to at least one embodiment of the present disclosure. A distal femur cutting block 100 of the present disclosure can be used by surgeons or other medical professionals to prepare a patient's distal femur for various types of knee surgery, such as the replacement of the medial joint and the patellofemoral joint, a total knee replacement, a unicompartmental replacement, and the like. As described herein, a distal femur cutting block 100 of the present disclosure is designed to fit over a portion of the distal femur and act as a guide for surgeons or other medical professionals when performing full or partial knee replacement surgeries.

The size and shape of the distal femur cutting block 100 according to the present disclosure are based upon the size and shape of the implant for the knee procedure. In at least one embodiment, the size and shape of the distal femur cutting block 100 according to the present disclosure may be chosen based upon the results of a CT scan and/or MRI of the patient's distal femur. That is, the distal femur cutting block 100 according to the present disclosure can be customized to substantially match the outer surface of the patient's distal femur using results from CT scans and/or MRIs of the distal femur. In order to further reduce the chance for surgeon errors and improve patient outcomes, the location, orientation, number of, and configuration of guides for cuts and pin placements may also be determined based upon CT scans and/or MRIs of the patient's distal femur. By having all of the cuts performed with the guidance of a single distal femur cutting block 100 (instead of multiple blocks used sequentially to carry out the needed cuts), the errors associated with cutting the distal femur can be reduced and patient outcomes can be improved. A distal femur cutting block 100 of the present disclosure can improve the selection of a properly sized femoral implant, improve the ability of the implant to properly rotate (leading to a better range of motion for the patient), and decrease operative time since surgeons can rely on the distal femur cutting block 100 for guidance. A distal femur cutting block 100 according to the present disclosure may be formed of a variety of suitable materials, including, but not limited to, nylon.

As shown in FIG. 1, a distal femur cutting block 100 according to at least one embodiment of the present disclosure is a monolithic cutting block including anterior portion 110 with anterior surface 150, and distal portion 120 with distal surface 160. Anterior portion 110 and distal portion 120 are connected through hinge 130, which is formed of the same material as anterior portion 110 and distal portion 120. When hinge 130 is in a closed position, anterior portion 110 and distal portion 120 are substantially perpendicular to one another. However, in at least one embodiment of the present disclosure when hinge 130 is in a closed position anterior portion 110 and distal portion 120 may be arranged relative to each other in a relationship that is less than or greater than perpendicular.

Figure 2:
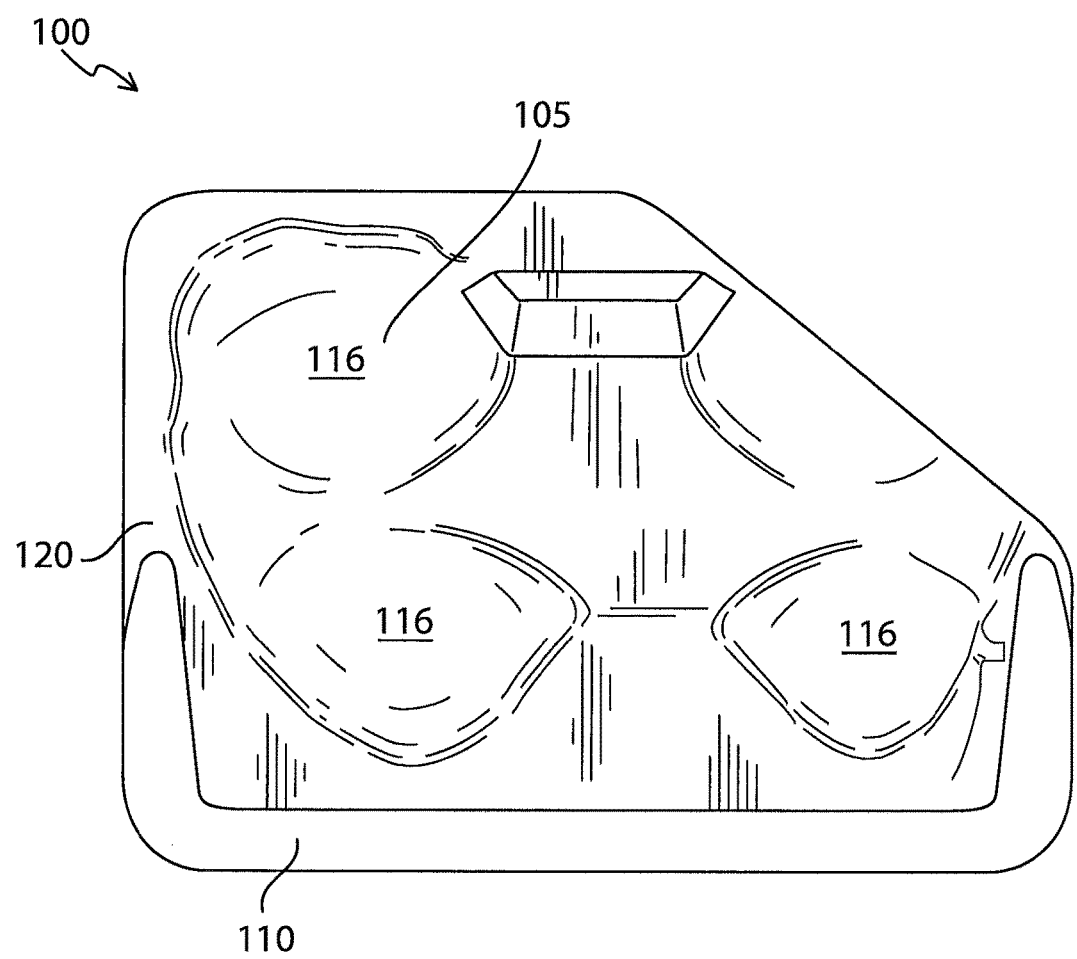
FIG. 2 shows a top view of a distal femur cutting block according to at least one embodiment of the present disclosure.

FIG. 2 shows a top view of a distal femur cutting block 100 according to at least one embodiment of the present disclosure. Shown in FIG. 2 is receiving portion 105 comprising the internal surfaces of anterior portion 110 and distal portion 120. Receiving portion 105 is configured to fit around the distal femur of a patient such that a surgeon or other medical professional can prepare the femur for receiving an implant. The internal surfaces of anterior portion 110 and distal portion 120 that form receiving portion 105 are contoured to fit snugly around the femoral condyles. Through the use of CT scans and/or MRIs, the contours of receiving portion 105 may be designed to closely match at least a portion of the femoral condyles.

Figure 3:
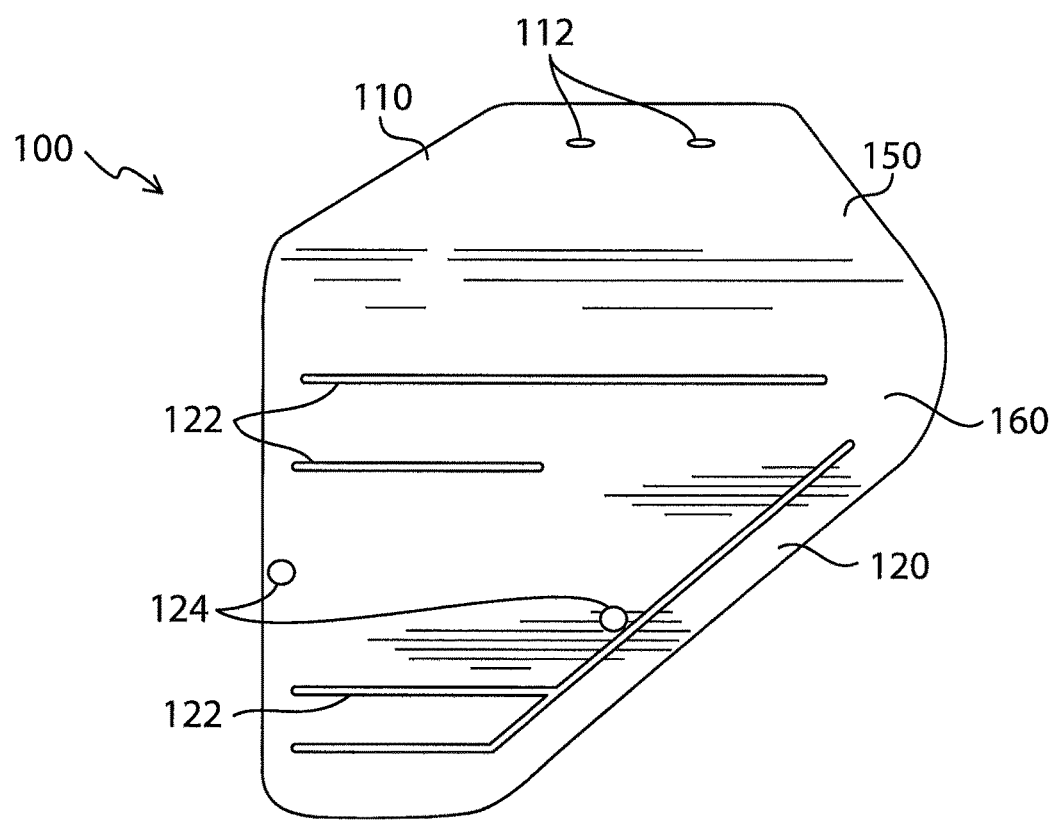
FIG. 3 shows a bottom perspective view of a distal femur cutting block according to at least one embodiment of the present disclosure.
Figure 4:
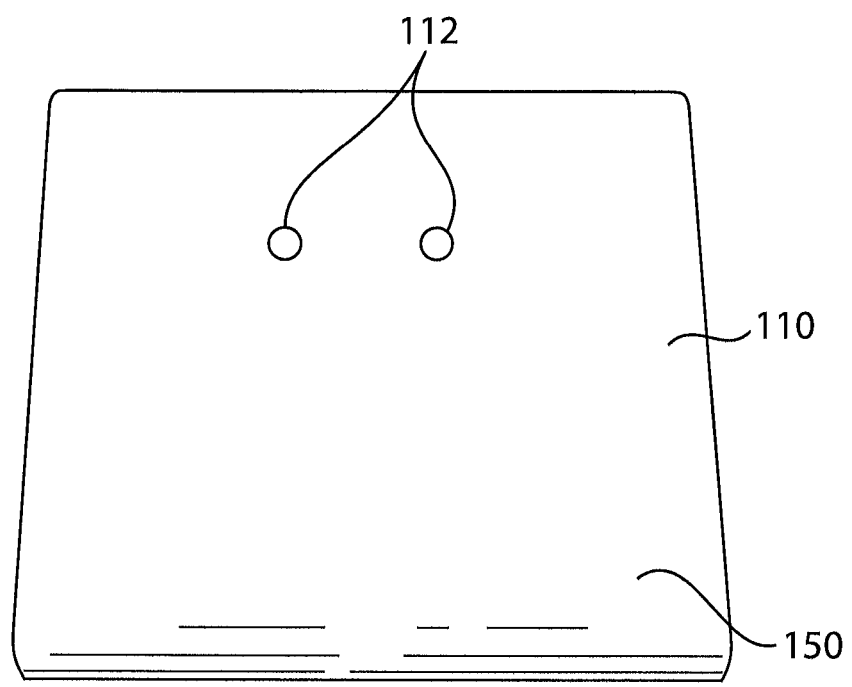
FIG. 4 shows a front view of a distal femur cutting block according to at least one embodiment of the present disclosure.

FIG. 3 shows a bottom perspective view of a distal femur cutting block 100 according to at least one embodiment of the present disclosure. FIG. 3 shows anterior portion 110 including anterior surface 150, and distal portion 120 including distal surface 160. As shown in FIG. 3, hinge 130 is in a closed position with anterior portion 110 and distal portion 120 at a substantially right angle. FIG. 4 shows a front view of a distal femur cutting block according to at least one embodiment of the present disclosure.

Shown in FIGS. 3-4 are pin guides 112 and 124. Pin guides 122 extend completely through anterior portion 110. Pin guides 124 extend completely through distal portion 120. In at least one embodiment, one or more of pin guides 112 and 124 may comprise a countersink configuration. As discussed herein, when distal femur cutting block 100 is positioned around a patient's distal femur, pins or screws may be inserted through pin guides 112 and 124 into the patient's distal femur in order to securely mount distal femur cutting block 100 to the patient's distal femur for a knee implant surgical procedure. Also shown in FIG. 3 are cutting guides 122. Cutting guides 122 extend through distal portion 120. In at least one embodiment, one or more cutting guides 122 may extend through distal portion 120 in an alignment that is substantially perpendicular to the bottom surface of distal portion 120. In at least one embodiment, one or more cutting guides 122 may extend through distal portion 120 in an alignment that is not perpendicular to the bottom surface of distal portion 120. As discussed herein, after distal femur cutting block 100 is positioned around and secured to a patient's distal femur, cutting instruments may be inserted through cutting guides 122 in order to accurately cut the femoral condyles into the shape needed to receive a knee implant. The placement of pin guides 112 and 124 and cutting guides 122 may be determined through the use of CT scans and/or MRI scans in order to ensure that once the block 100 is attached to the distal femur, the surgeon or other medical professional will have the correct locations to cut the femoral condyles and/or insert pins.

Figure 5:
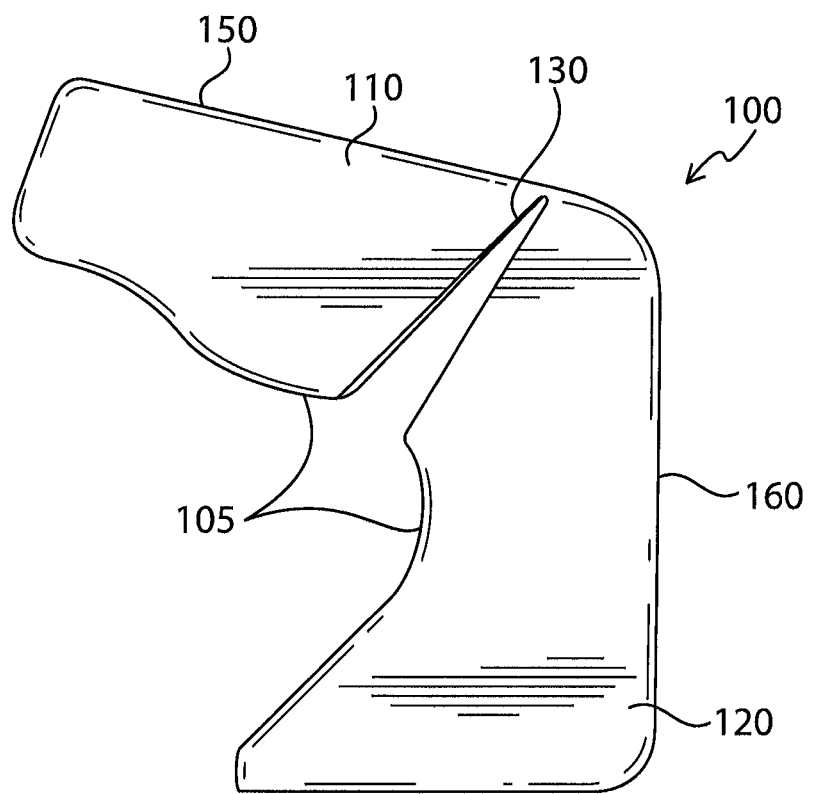
FIG. 5 shows a side view of a distal femur cutting block according to at least one embodiment of the present disclosure.
Figure 6:
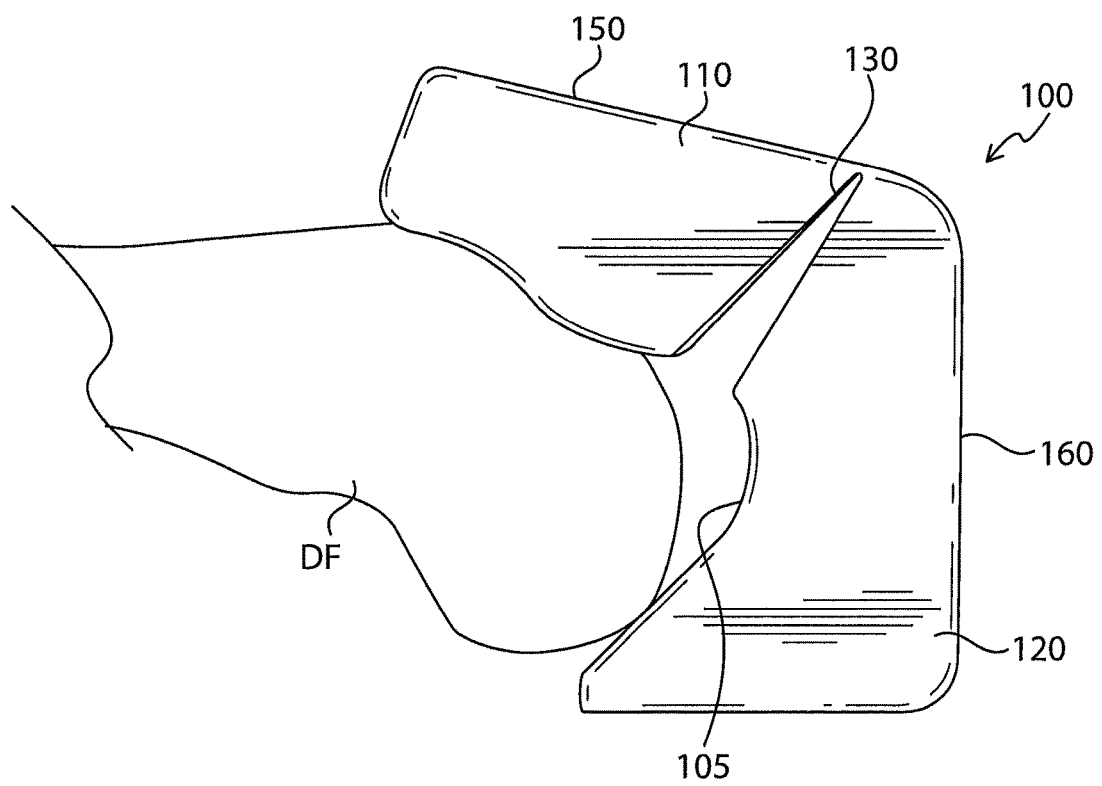
FIG. 6 shows a side view of a distal femur cutting block according to at least one embodiment of the present disclosure in the presence of a distal femur.
Figure 7:
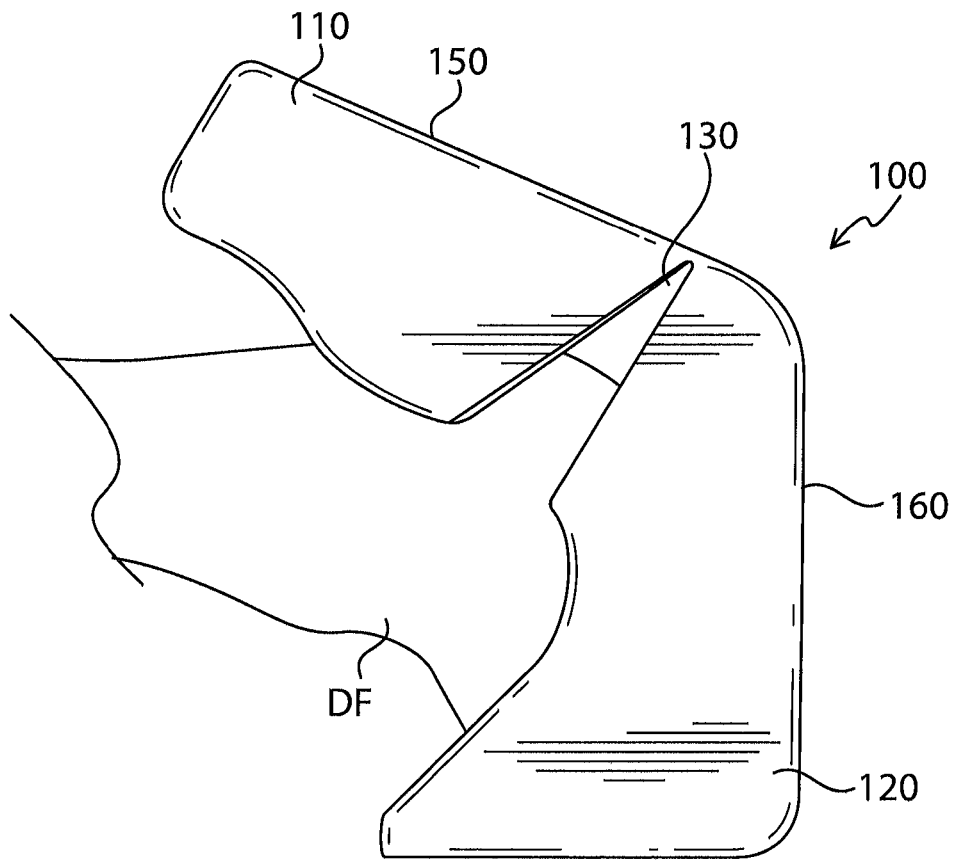
FIG. 7 shows a side view of a distal femur cutting block according to at least one embodiment of the present disclosure in the presence of a distal femur.
Figure 8:
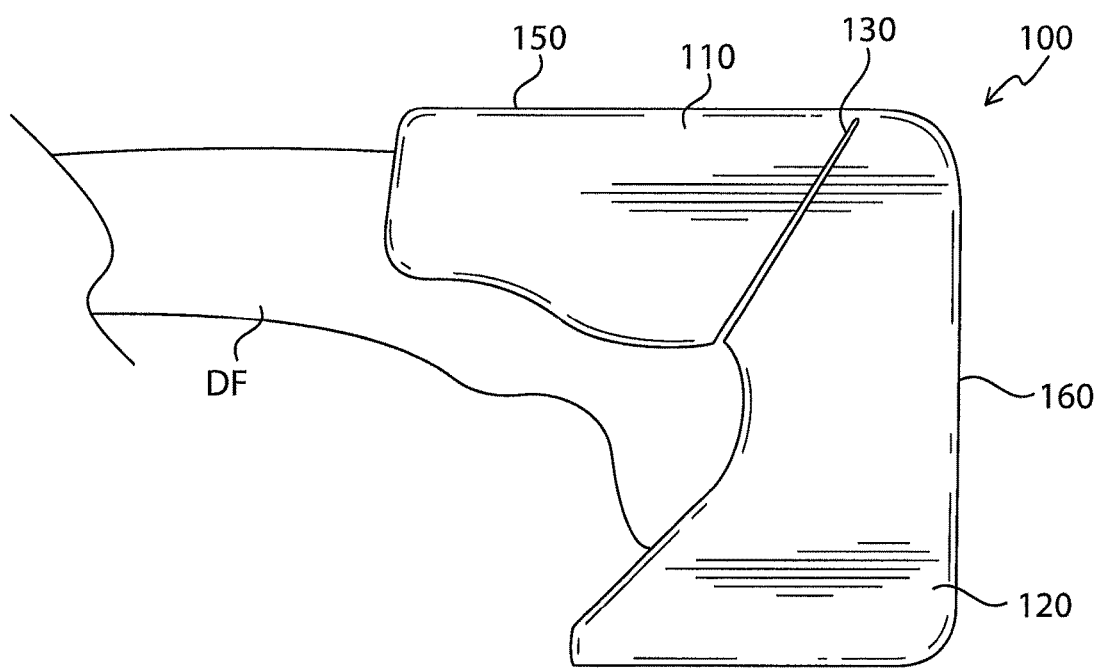
FIG. 8 shows a side view of a distal femur cutting block according to at least one embodiment of the present disclosure in the presence of a distal femur.

FIGS. 5-10 show a step-by-step process of applying distal femur cutting block 100 to a distal femur DF, according to at least one embodiment of the present disclosure. As shown in FIG. 5, anterior portion 110 and distal portion 120 are rotated relative to one another around hinge 130 to form an open configuration such that the distal femur DF can be received within the receiving portion 105 of distal femur cutting block 100. As shown in FIGS. 6-7, distal femur DF is inserted within the receiving portion 105 of the distal femur cutting block 100, which is still in the flexed configuration. As shown in FIG. 8, anterior portion 110 and distal portion 120 are rotated relative to one another around hinge 130 to close anterior portion 110 and distal portion 120 around distal femur cutting block 100 around distal femur DF. As shown in FIG. 8, hinge. 130 is in a closed position and anterior portion 110 and distal portion 120 are substantially perpendicular to one another.

Figure 9:
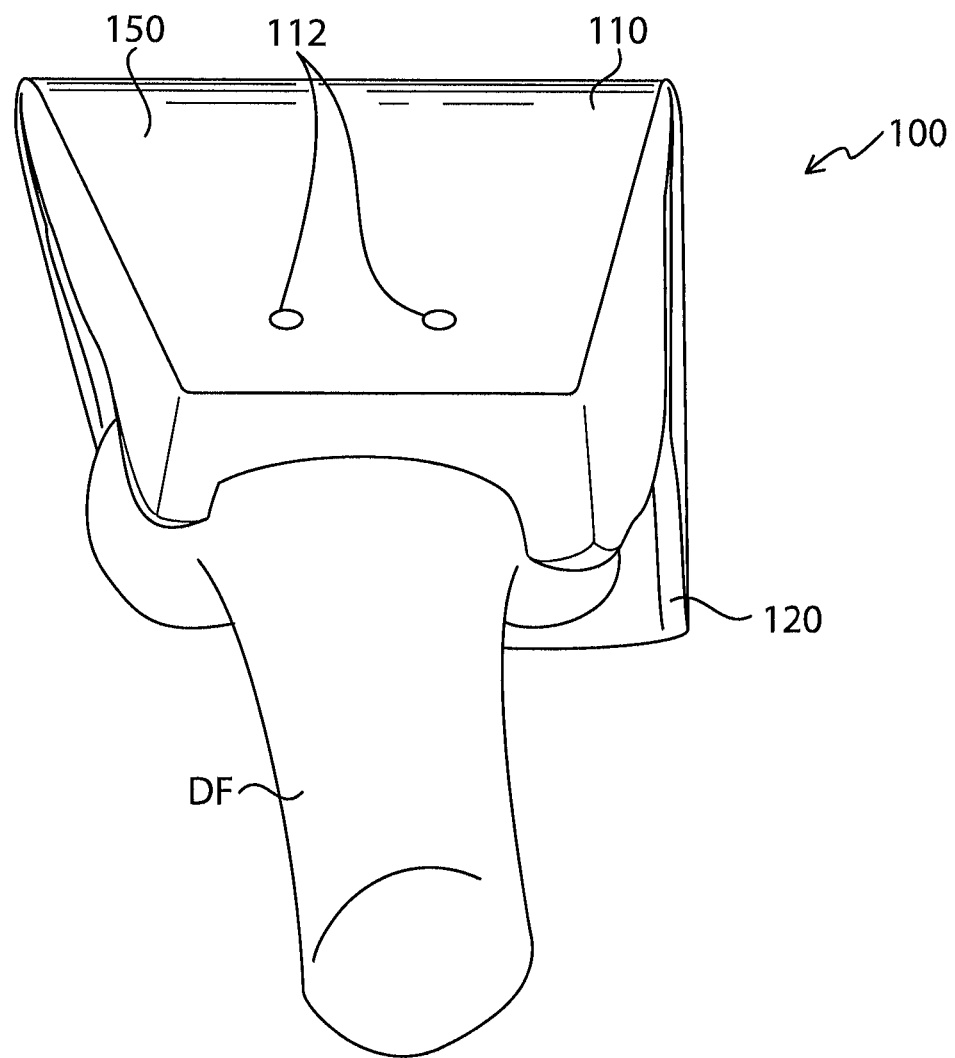
FIG. 9 shows a top perspective view of a distal femur cutting block according to at least one embodiment of the present disclosure in the presence of a distal femur.

FIG. 9 shows a top perspective view of a distal femur cutting block 100 according to at least one embodiment of the present disclosure closed around a distal femur. After distal femur cutting block 100 is closed around a distal femur, pins or screws may be inserted through pin guides 112 into the patient's distal femur in order to securely mount distal femur cutting block 100 to the patient's distal femur for a knee implant surgical procedure.

Figure 10:
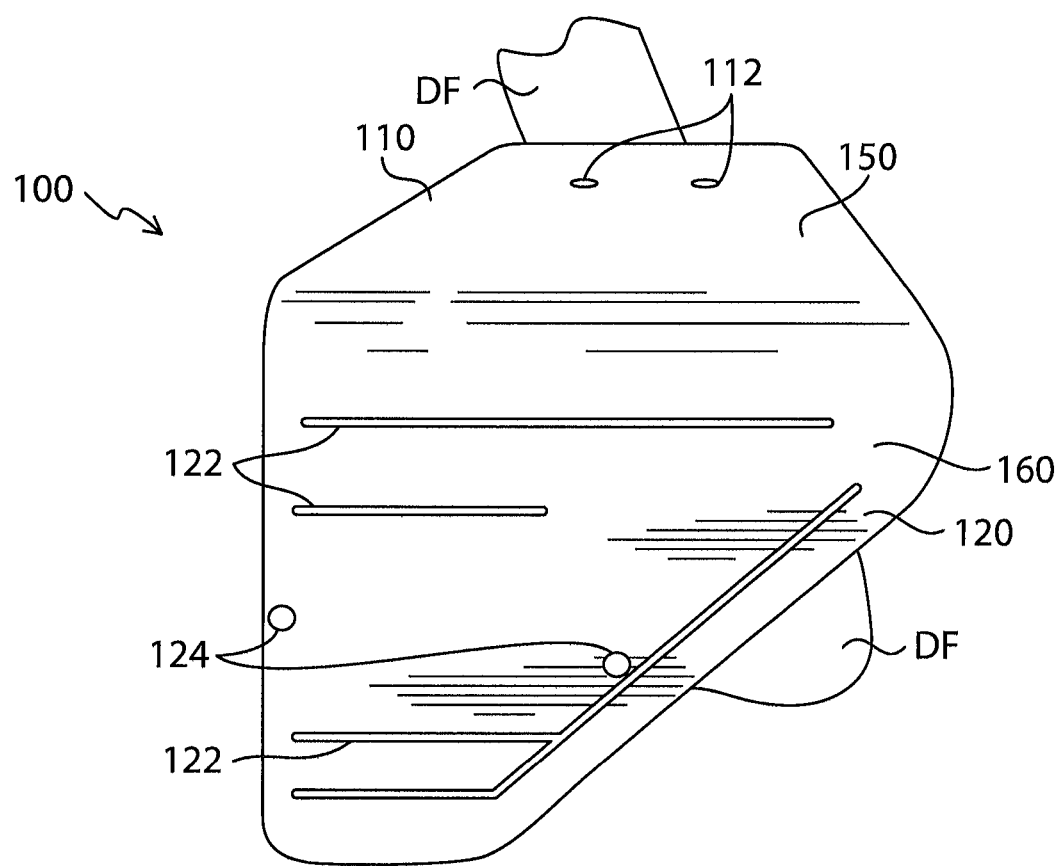
FIG. 10 shows a bottom perspective view of a distal femur cutting block according to at least one embodiment of the present disclosure in the presence of a distal femur.

FIG. 10 shows a bottom perspective view of a distal femur cutting block 100 according to at least one embodiment of the present disclosure closed around a distal femur. After distal femur cutting block 100 is closed around a distal femur, pins or screws may be inserted through pin guides 124 into the patient's distal femur in order to securely mount distal femur cutting block 100 to the patient's distal femur for a knee implant surgical procedure. As discussed herein, after distal femur cutting block 100 is positioned around a patient's distal femur and after distal femur cutting block 100 is secured to a patient's distal femur by pins or screws inserted through pin guides 112 and 124 into the patient's distal femur, cutting instruments may be inserted through cutting guides 122 in order to accurately cut the femoral condyles into the shape needed to receive a knee implant. Such cuts may include one or more of posterior cut, posterior chamber cut, anterior chamber cut, anterior cut, distal femoral cut, and transition cut.

Figure 11:
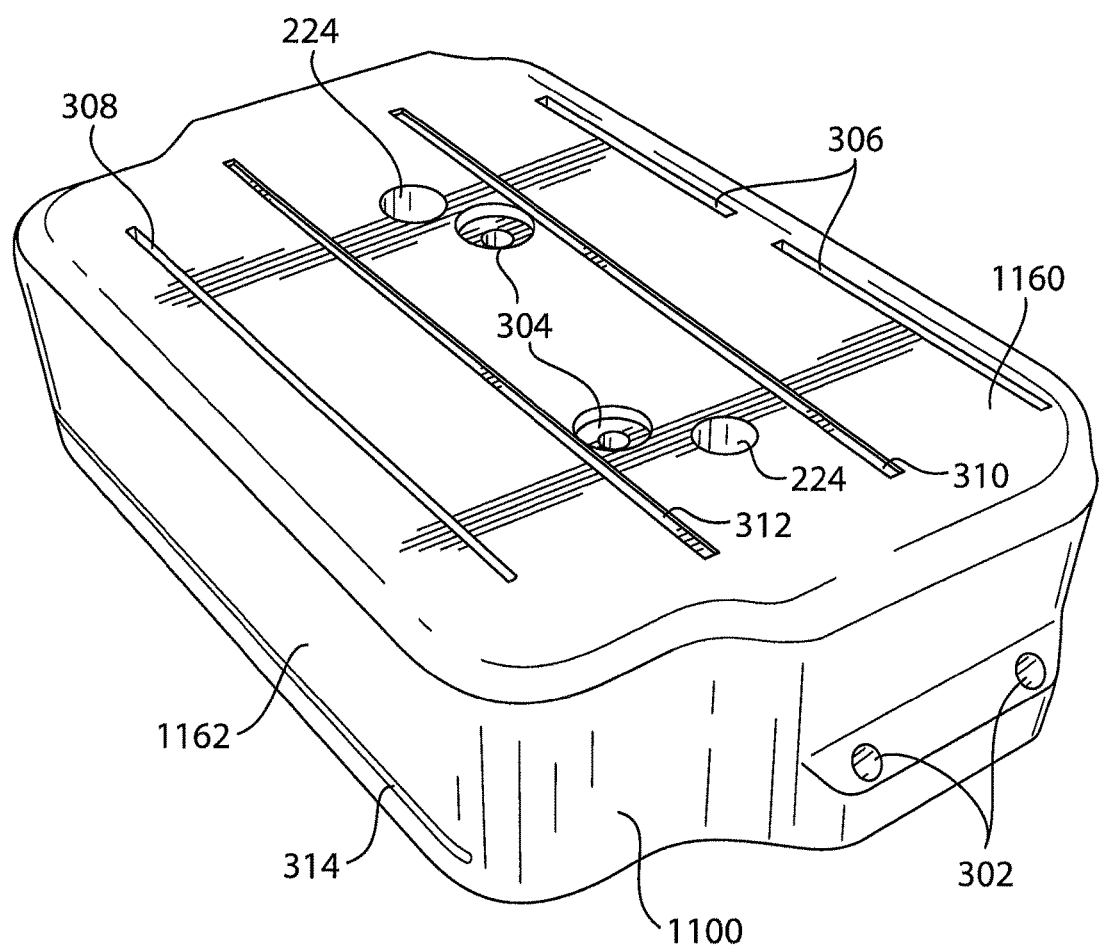
FIG. 11 shows a bottom perspective view of a distal femur cutting block according to at least one embodiment of the present disclosure.

FIG. 11 shows a bottom perspective view of a distal femur cutting block 1100 according to at least one embodiment of the present disclosure. A distal femur cutting block 1100 according to the present disclosure may be formed of a variety of suitable materials, including, but not limited to, nylon. Shown in FIG. 11 are pin guides 302 and 304. Pin guides 302 and 304 extend completely through distal femur cutting block 1100. In at least one embodiment, one or more of pin guides 302 and 304 may comprise a countersink configuration. When distal femur cutting block 1100 is positioned on a patient's distal femur, pins or screws may be inserted through pin guides 302 and 304 into the patient's distal femur in order to securely mount distal femur cutting block 1100 to the patient's distal femur for a knee implant surgical procedure. Also shown in FIG. 11 are cutting guides 224, 306, 308, 310, 312, and 314. Cutting guides 224, 306, 308, 310, 312, and 314 extend through distal femur cutting block 1100. In at least one embodiment, one or more of cutting guides 224, 306, and 308 may extend through distal femur cutting block 1100 in an alignment that is substantially perpendicular to bottom surface 1160 of distal femur cutting block 1100. In at least one embodiment, one or more of cutting guides 310 and 312 may extend through distal femur cutting block 1100 in an alignment that is not perpendicular to the bottom surface 1160 of distal femur cutting block 1100. In at least one embodiment, cutting guide 314 may extend through distal femur cutting block 1100 in an alignment that is substantially perpendicular to front surface 1162 of distal femur cutting block 1100. As discussed herein, after distal femur cutting block 1100 is positioned on and secured to a patient's distal femur, cutting instruments may be inserted thorough cutting guides 224, 306, 308, 310, 312, and 314 in order to accurately cut the femoral condyles into the shape needed to receive a knee implant, or to accurately drill holes into the femoral condyles to facilitate attachment of a knee implant. The placement of pin guides 302 and 304, and cutting guides 224, 306, 308, 310, 312, and 314 may be determined through the use of CT scans and/or MRI scans in order to ensure that once distal femur cutting block 1100 is attached to the distal femur, the surgeon or other medical professional will have the correct locations to cut the femoral condyles and/or insert pins. By having all of the cuts performed with the guidance of a single distal femur cutting block 1100 (instead of multiple blocks used sequentially to carry out the needed cuts), the errors associated with cutting the distal femur can be reduced and patient outcomes can be improved.

Figure 12:
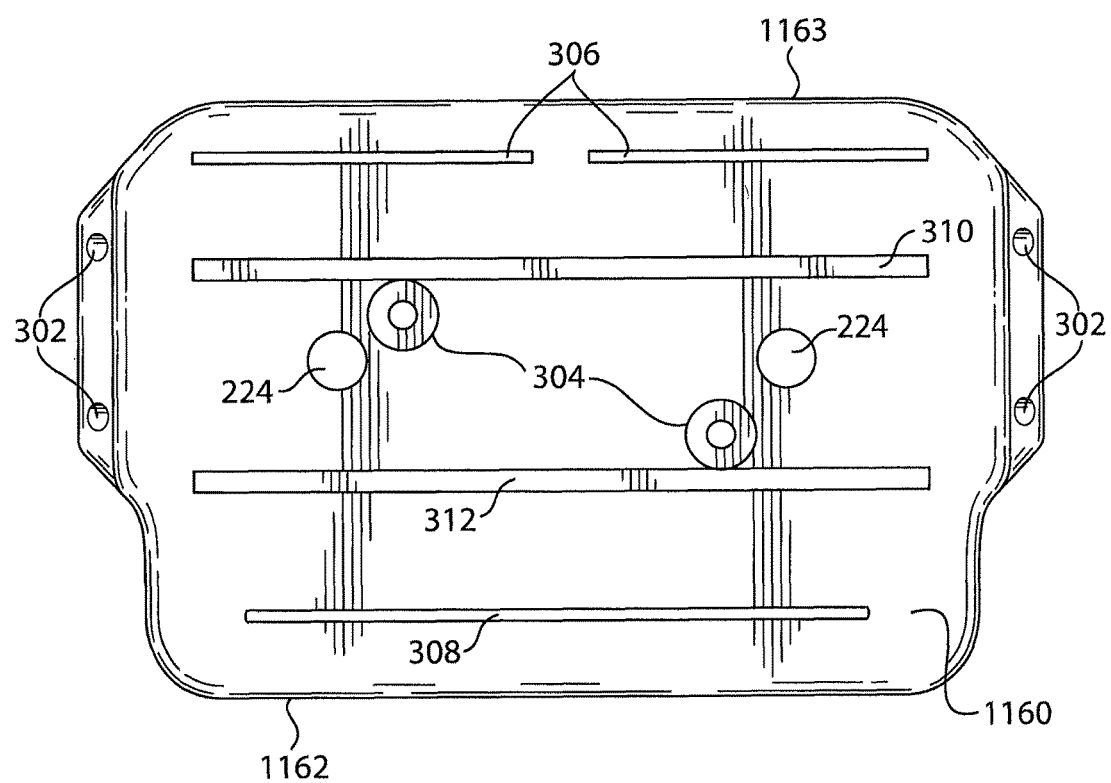
FIG. 12 shows a bottom view of a distal femur cutting block according to at least one embodiment of the present disclosure.

FIG. 12 shows a bottom view of a distal femur cutting block 1100 according to at least one embodiment of the present disclosure, including front surface 1162 and rear surface 1163. Shown in FIG. 12 are pin guides 302 and 304, and cutting guides 224, 306, 308, 310, and 312.

Figure 13:
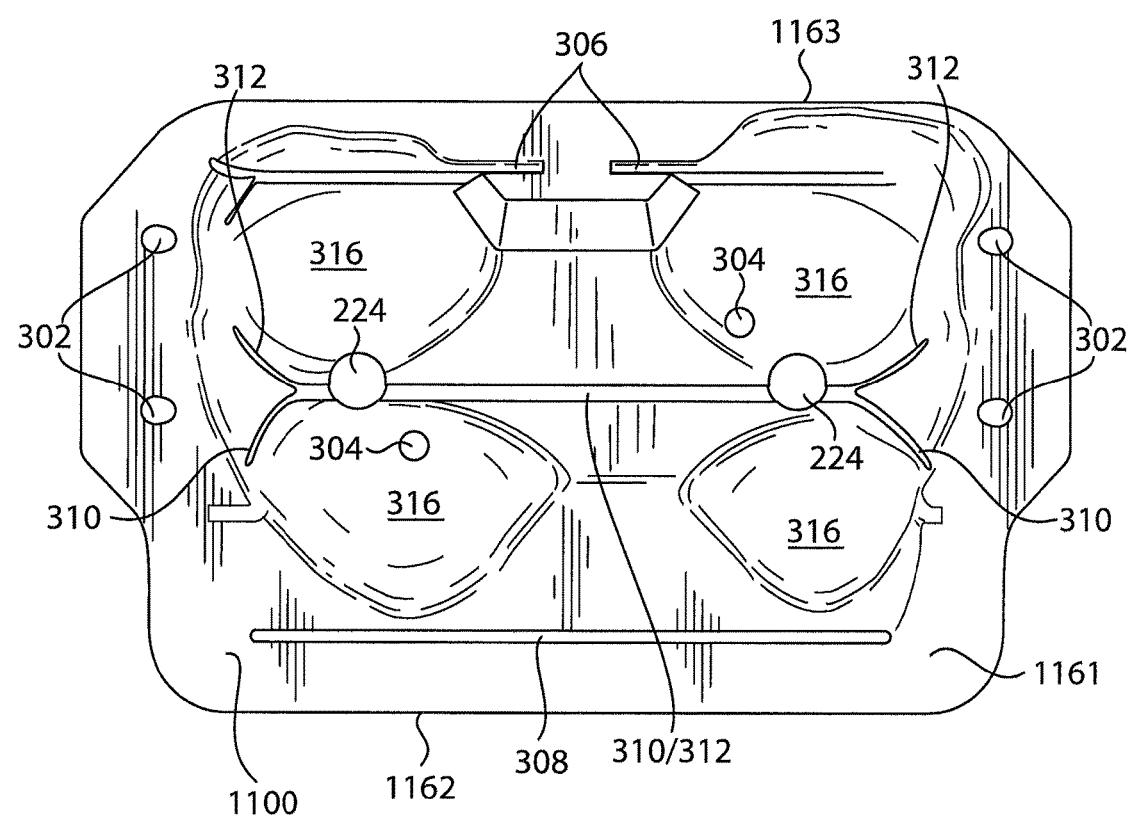
FIG. 13 shows a top view of a distal femur cutting block according to at least one embodiment of the present disclosure.

FIG. 13 shows a top view of a distal femur cutting block 1100 according to at least one embodiment of the present disclosure, including top surface 1161, front surface 1162, and rear surface 1163. Shown in FIG. 13 are pin guides 302 and 304, and cutting guides 224, 306, 308, 310, and 312. Also shown in FIG. 13 are impressions 316. Impressions 316 comprise contoured portions of the top surface 1161 of distal femur cutting block 1100. Impressions 316 are contoured to fit against the femoral condyles. Through the use of CT scans and/or MRIs, the contours of impressions 316 may be configured to closely match at least a portion of the femoral condyles.

Figure 14:
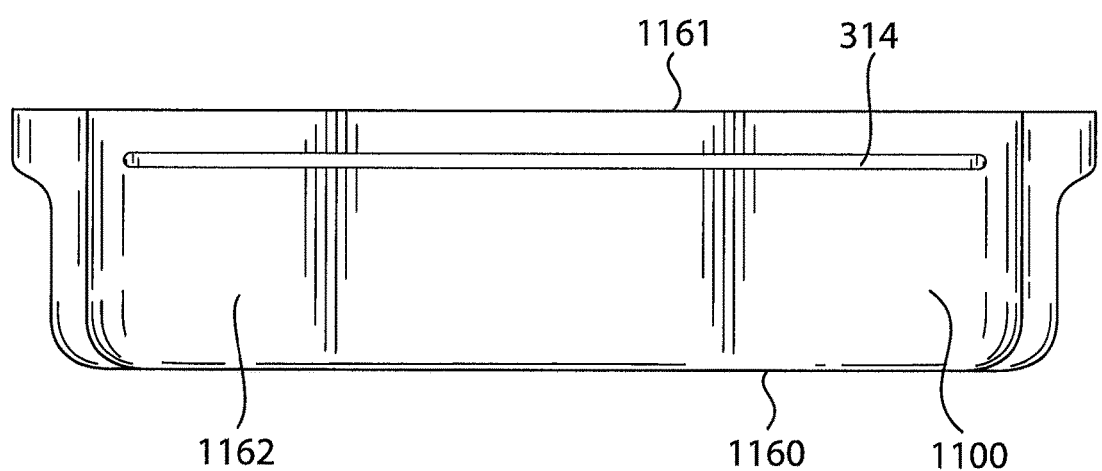
FIG. 14 shows an anterior view of a distal femur cutting block according to at least one embodiment of the present disclosure.

FIG. 14 shows an anterior view of a distal femur cutting block 1100 according to at least one embodiment of the present disclosure. Shown in FIG. 14 is front surface 1162 with cutting guide 314 extending therethrough.

Figure 15:
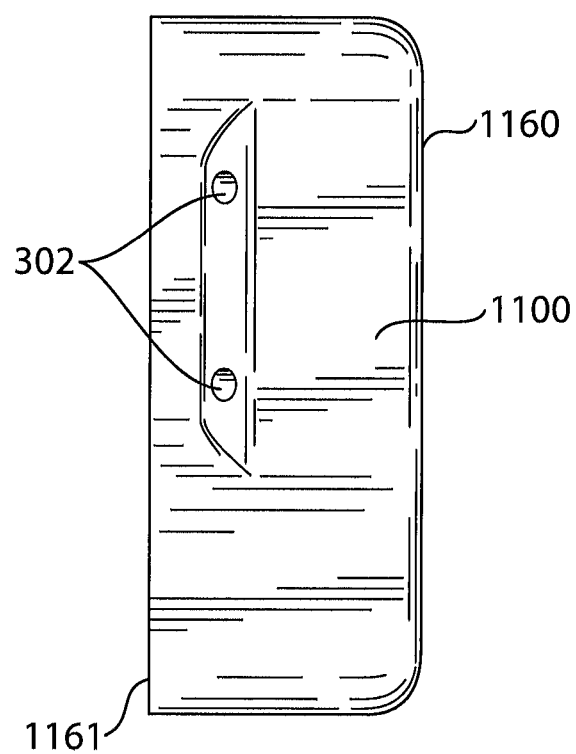
FIG. 15 shows an end view of a distal femur cutting block according to at least one embodiment of the present disclosure.

FIG. 15 shows an end view of a distal femur cutting block 1100 according to at least one embodiment of the present disclosure. Shown in FIG. 14 are pin guides 302.

Figure 16:
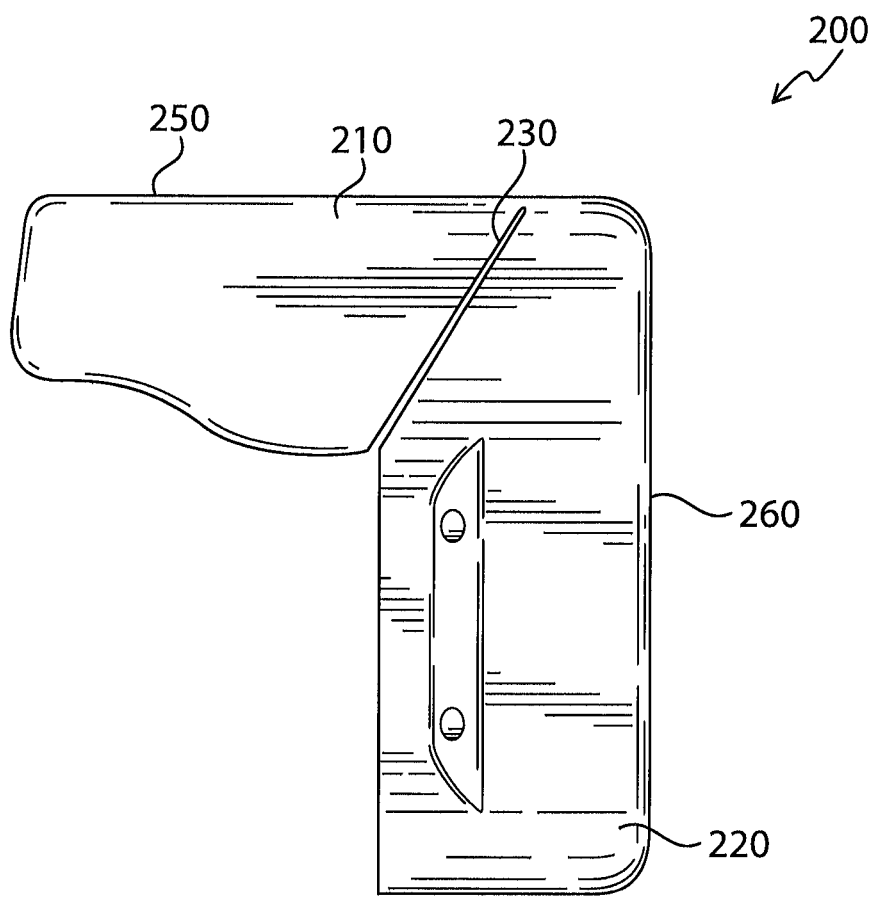
FIG. 16 shows a side view of a distal femur cutting block according to at least one embodiment of the present disclosure.

FIG. 16 shows a distal femur cutting block 200 according to at least one embodiment of the present disclosure. As described herein, a distal femur cutting block 200 of the present disclosure is designed to fit over a portion of the distal femur and act as a guide for surgeons or other medical professionals when performing full knee replacement surgeries.

The size and shape of the distal femur cutting block 200 according to the present disclosure are based upon the size and shape of the implant for the knee procedure. In at least one embodiment, the size and shape of the distal femur cutting block 200 according to the present disclosure may be chosen based upon the results of a CT scan and/or MRI of the patient's distal femur. That is, the distal femur cutting block 200 according to the present disclosure can be customized to substantially match the outer surface of the patient's distal femur using results from CT scans and/or MRIs of the distal femur. In order to further reduce the chance for surgeon errors and improve patient outcomes, the location, orientation, number of, and configuration of guides for cuts and pin placements may also be determined based upon CT scans and/or MRIs of the patient's distal femur. By having all of the cuts performed with the guidance of a single distal femur cutting block 200 (instead of multiple blocks used sequentially to carry out the needed cuts), the errors associated with cutting the distal femur can be reduced and patient outcomes can be improved. A distal femur cutting block 200 of the present disclosure can improve the selection of a properly sized femoral implant, improve the ability of the implant to properly rotate (leading to a better range of motion for the patient), and decrease operative time since surgeons can rely on the distal femur cutting block 200 for guidance. A distal femur cutting block 200 according to the present disclosure may be formed of a variety of suitable materials, including, but not limited to, nylon.

As shown in FIG. 16, a distal femur cutting block 200 according to at least one embodiment of the present disclosure is a monolithic cutting block including anterior portion 210 with anterior surface 250, and distal portion 220 with distal surface 260. Anterior portion 210 and distal portion 220 are connected through hinge 230, which is formed of the same material as anterior portion 210 and distal portion 220. When hinge 230 is in a closed position, anterior portion 210 and distal portion 220 are substantially perpendicular to one another. However, in at least one embodiment of the present disclosure when hinge 230 is in a closed position anterior portion 210 and distal portion 220 may be arranged relative to each other in a relationship that is less than or greater than perpendicular.

Figure 17:
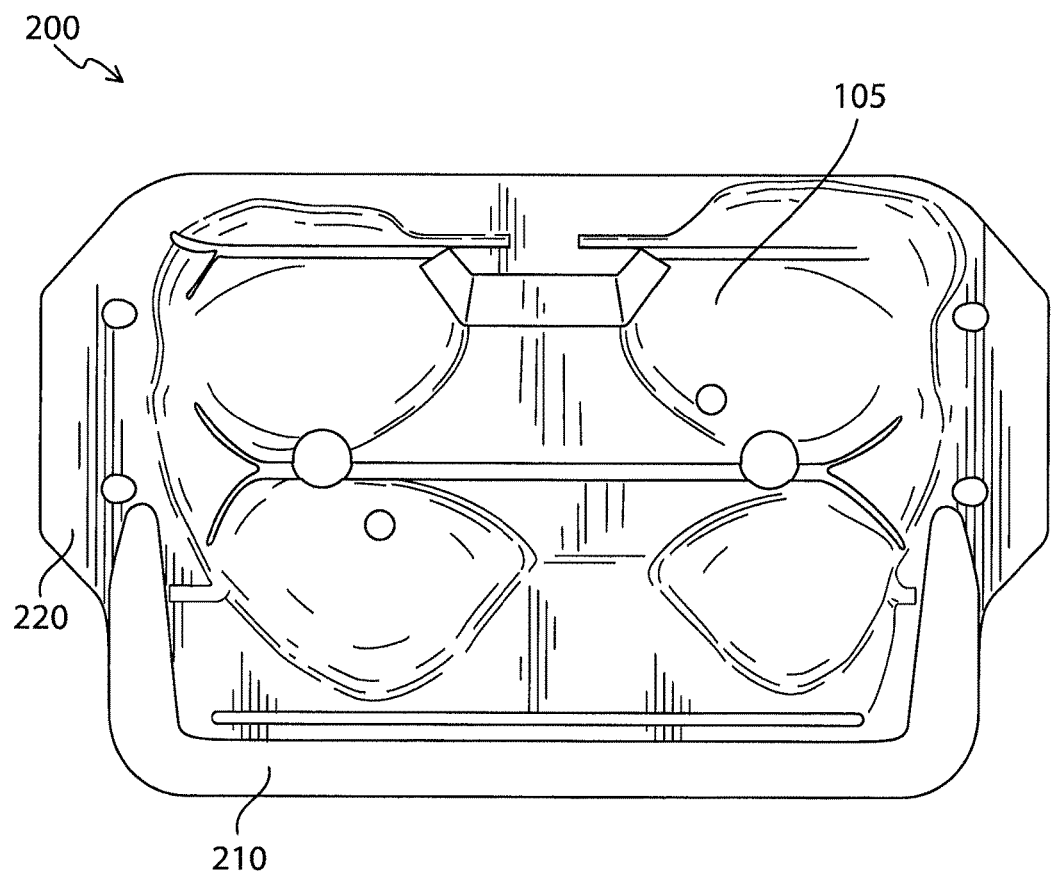
FIG. 17 shows a top view of a distal femur cutting block according to at least one embodiment of the present disclosure.

FIG. 17 shows a top view of a distal femur cutting block 200 according to at least one embodiment of the present disclosure. Shown in FIG. 17 is receiving portion 205 comprising the internal surfaces of anterior portion 210 and distal portion 220. Receiving portion 205 is configured to fit around the distal femur of a patient such that a surgeon or other medical professional can prepare the femur for receiving an implant. The internal surfaces of anterior portion 210 and distal portion 220 that form receiving portion 205 are contoured to fit snugly around the femoral condyles. Through the use of CT scans and/or MRIs, the contours of receiving portion 205 may be designed to closely match at least a portion of the femoral condyles.

Figure 18:
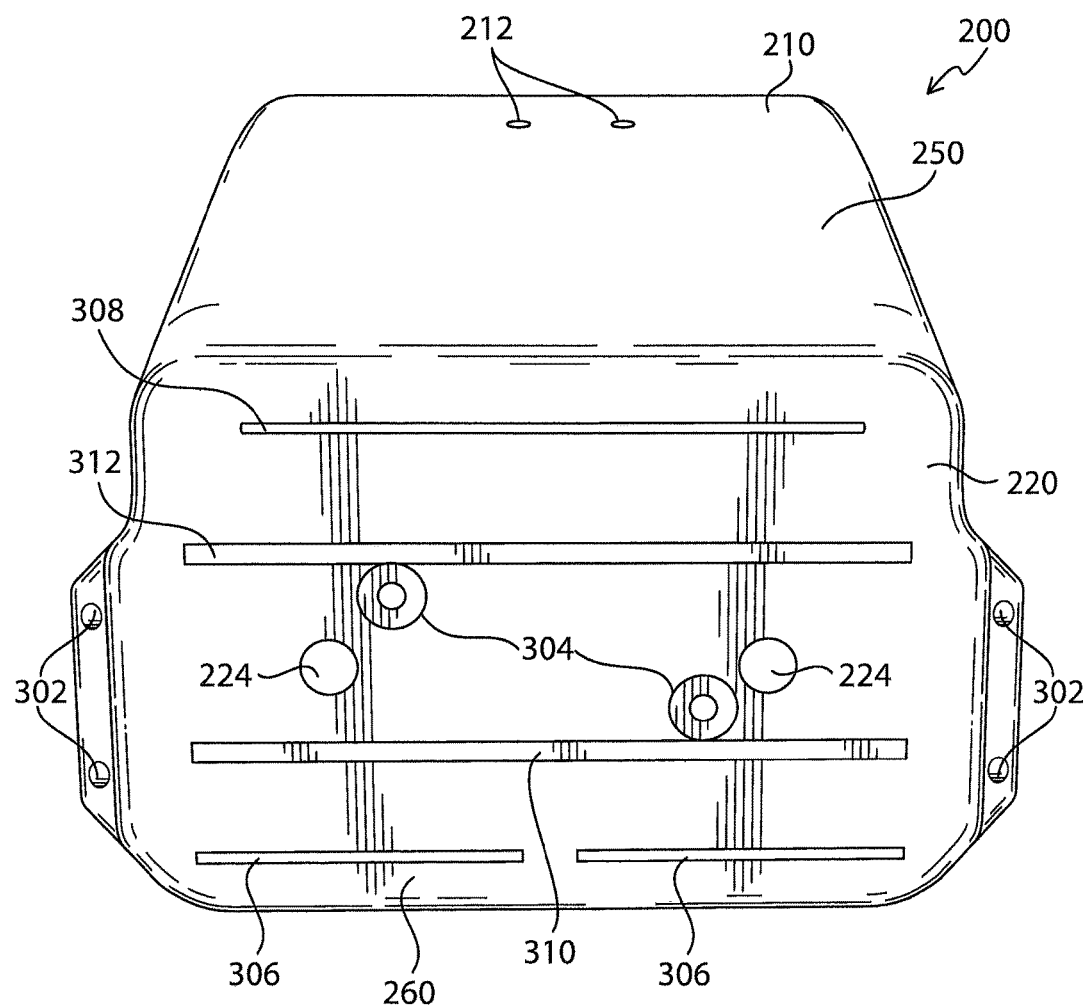
FIG. 18 shows a bottom perspective view of a distal femur cutting block according to at least one embodiment of the present disclosure.
Figure 19:
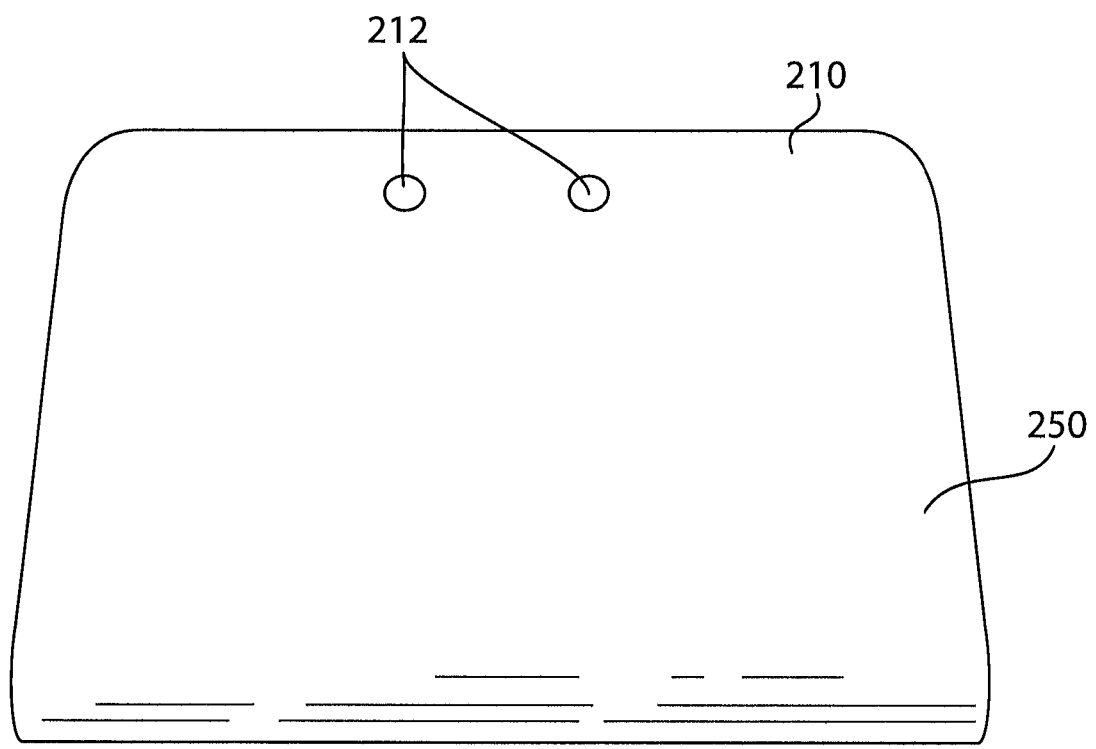
FIG. 19 shows a front view of a distal femur cutting block according to at least one embodiment of the present disclosure.

FIG. 18 shows a bottom perspective view of a distal femur cutting block 200 according to at least one embodiment of the present disclosure. FIG. 18 shows anterior portion 210 including anterior surface 250, and distal portion 220 including distal surface 260. As shown in FIG. 18, hinge 230 is in a closed position with anterior portion 210 and distal portion 220 at a substantially right angle. FIG. 19 shows a front view of a distal femur cutting block according to at least one embodiment of the present disclosure.

Shown in FIGS. 18-19 are pin guides 212, 302, and 304. Pin guides 212 extend completely through anterior portion 210. Pin guides 302 and 304 extend completely through distal portion 220. In at least one embodiment, one or more of pin guides 212, 302, and 304 may comprise a countersink configuration. As discussed herein, when distal femur cutting block 200 is positioned around a patient's distal femur, pins or screws may be inserted through pin guides 212, 302, and 304 into the patient's distal femur in order to securely mount distal femur cutting block 200 to the patient's distal femur for a knee implant surgical procedure. Also shown in FIG. 18 are cutting guides 224, 306, 308, 310, and 312. Cutting guides 224, 306, 308, 310, and 312 extend through distal portion 220. In at least one embodiment, cutting guides 224, 306, and 308 may extend through distal portion 220 in an alignment that is substantially perpendicular to the bottom surface of distal portion 220. In at least one embodiment, a cutting guides 310 and 312 may extend through distal portion 220 in an alignment that is not perpendicular to the bottom surface of distal portion 220. As discussed herein, after distal femur cutting block 200 is positioned around and secured to a patient's distal femur, cutting instruments may be inserted through cutting guides 224, 306, 308, 310, and 312 in order to accurately cut the femoral condyles into the shape needed to receive a knee implant, or to accurately drill holes into the femoral condyles to facilitate attachment of a knee implant. The placement of pin guides 212, 302, and 304, and cutting guides 224, 306, 308, 310, and 312 may be determined through the use of CT scans and/or MRI scans in order to ensure that once the block 200 is attached to the distal femur, the surgeon or other medical professional will have the correct locations to cut the femoral condyles and/or insert pins.

Figure 20:
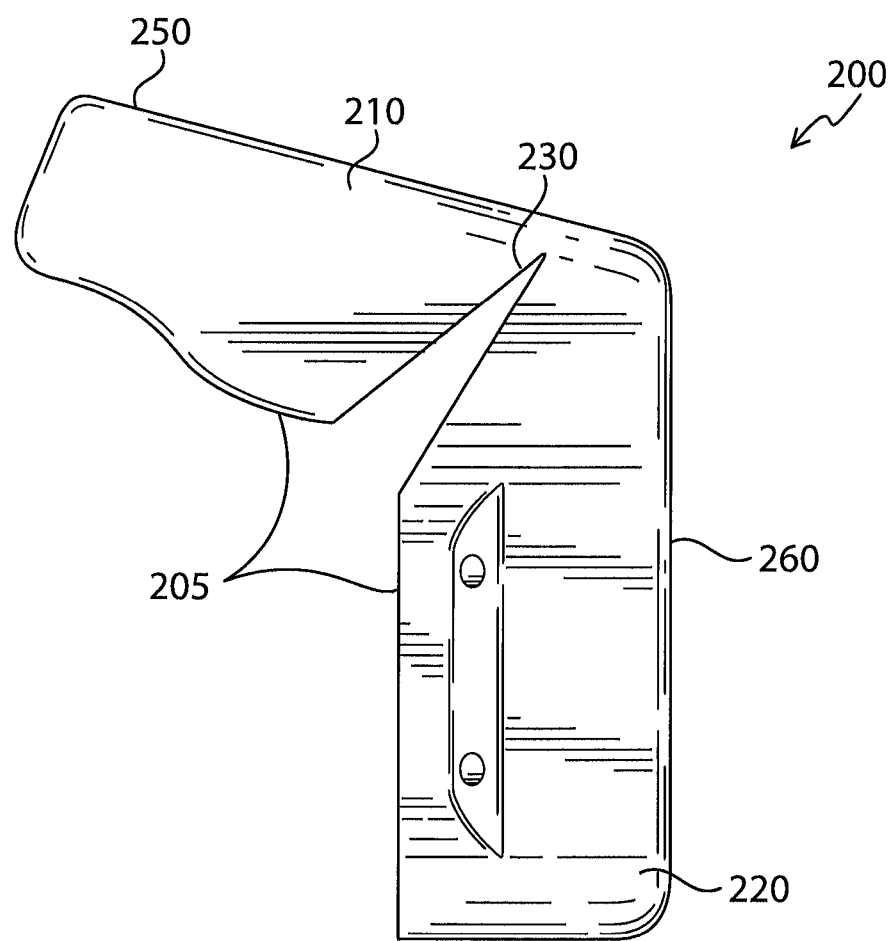
FIG. 20 shows a side view of a distal femur cutting block according to at least one embodiment of the present disclosure.
Figure 21:
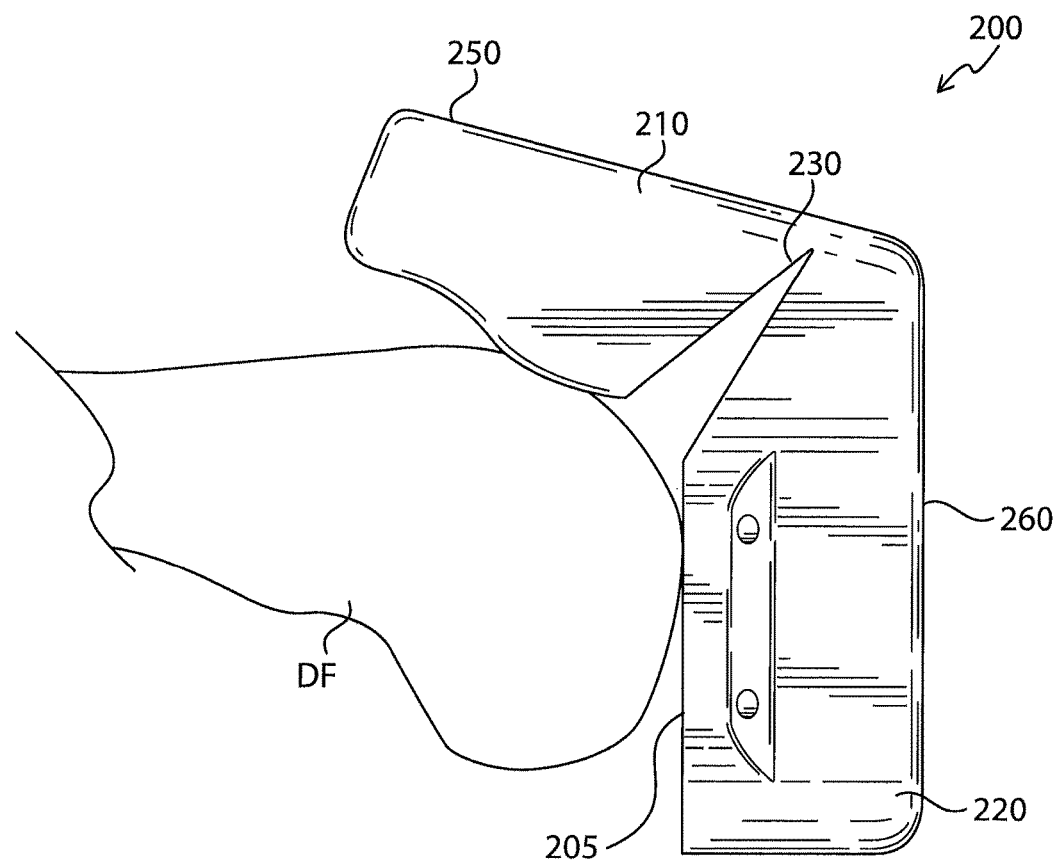
FIG. 21 shows a side view of a distal femur cutting block according to at least one embodiment of the present disclosure in the presence of a distal femur.
Figure 22:
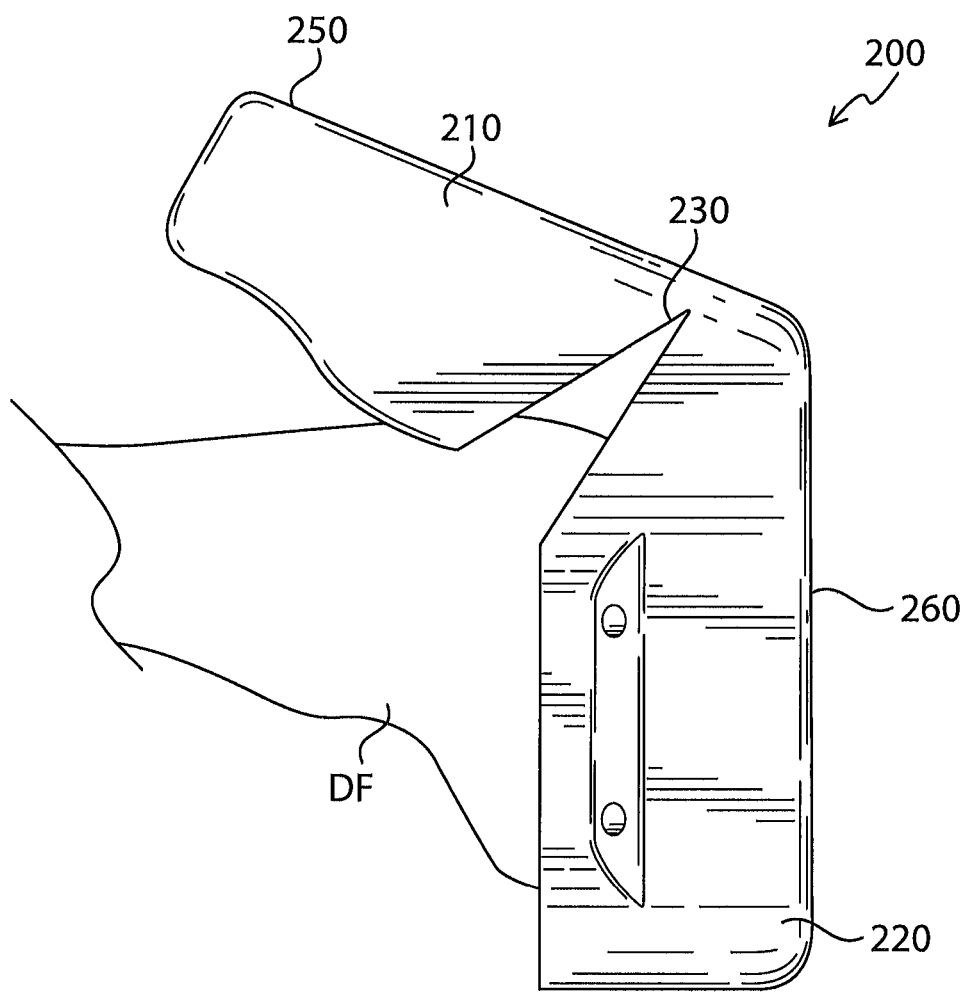
FIG. 22 shows a side view of a distal femur cutting block according to at least one embodiment of the present disclosure in the presence of a distal femur.
Figure 23:
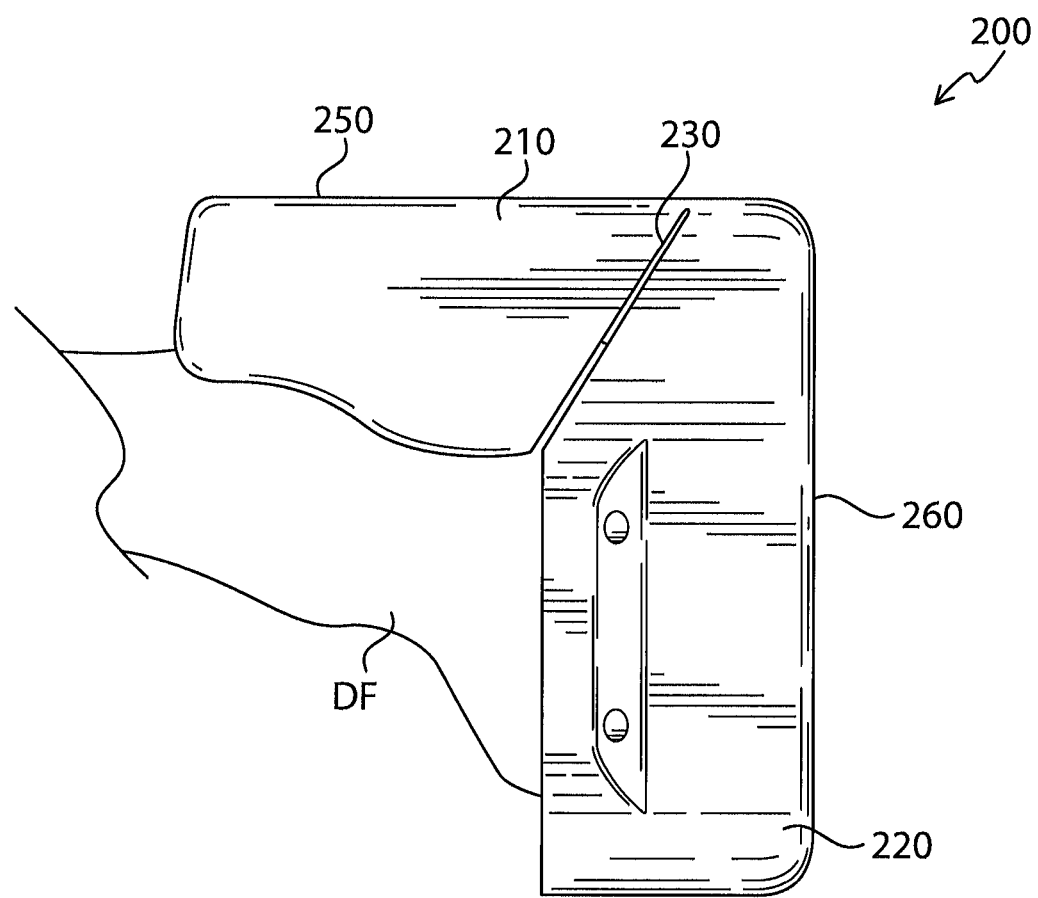
FIG. 23 shows a side view of a distal femur cutting block according to at least one embodiment of the present disclosure in the presence of a distal femur.

FIGS. 20-25 show a step-by-step process of applying distal femur cutting block 200 to a distal femur DF, according to at least one embodiment of the present disclosure. As shown in FIG. 20, anterior portion 210 and distal portion 220 are rotated relative to one another around hinge 230 to form an open configuration such that the distal femur DF can be received within the receiving portion 205 of distal femur cutting block 200. As shown in FIGS. 21-22, distal femur DF is inserted within the receiving portion 205 of the distal femur cutting block 200, which is still in the flexed configuration. As shown in FIG. 23, anterior portion 210 and distal portion 220 are rotated relative to one another around hinge 230 distal femur cutting block 200 around distal femur DF. As shown in FIG. 23, hinge 230 is in a closed position and anterior portion 210 and distal portion 220 are substantially perpendicular to one another.

Figure 24:
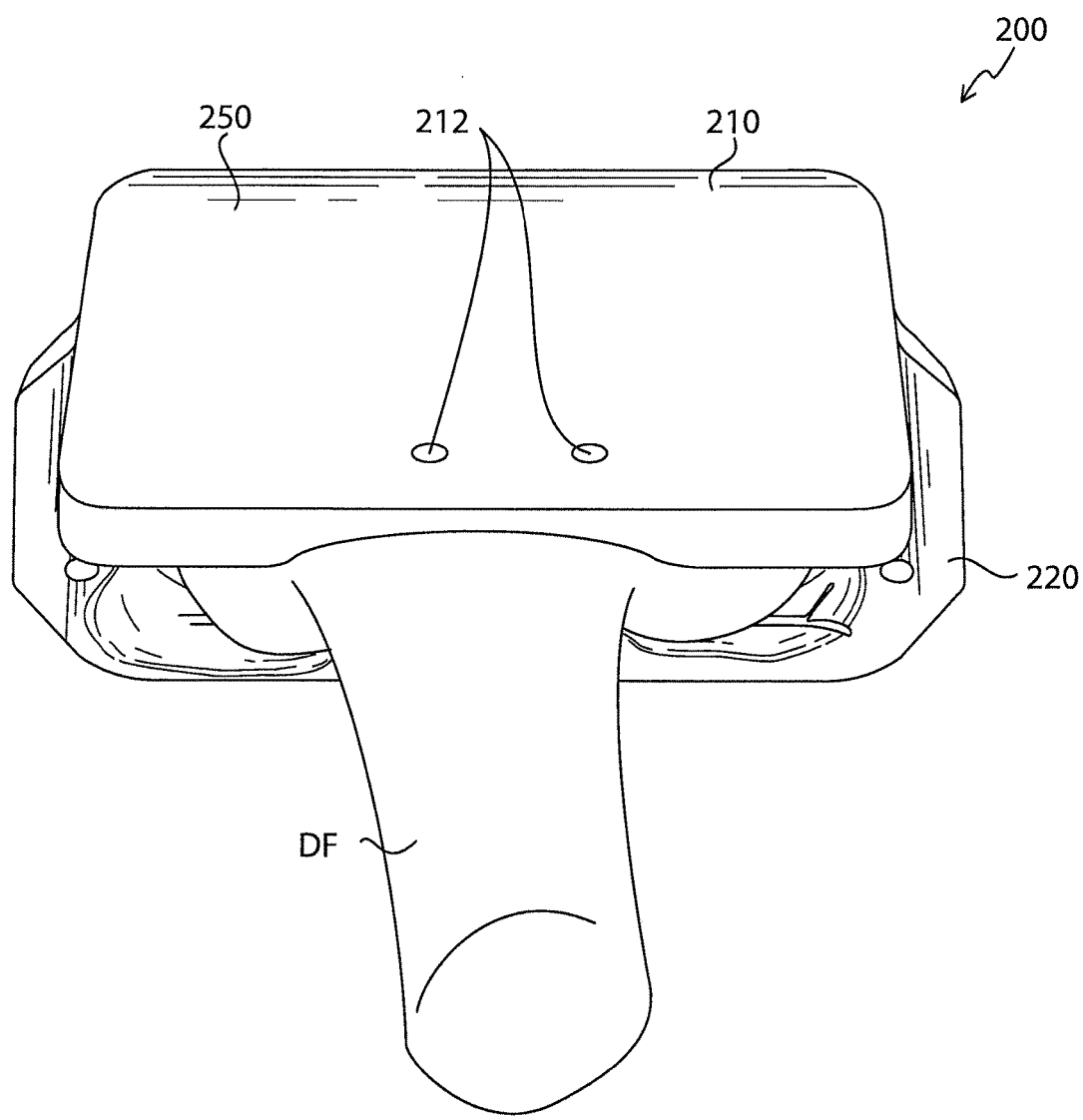
FIG. 24 shows a top perspective view of a distal femur cutting block according to at least one embodiment of the present disclosure in the presence of a distal femur.

FIG. 24 shows a top perspective view of a distal femur cutting block 200 according to at least one embodiment of the present disclosure closed around a distal femur. After distal femur cutting block 200 is closed around a distal femur, pins or screws may be inserted through pin guides 212 into the patient's distal femur in order to securely mount distal femur cutting block 200 to the patient's distal femur for a knee implant surgical procedure.

Figure 25:
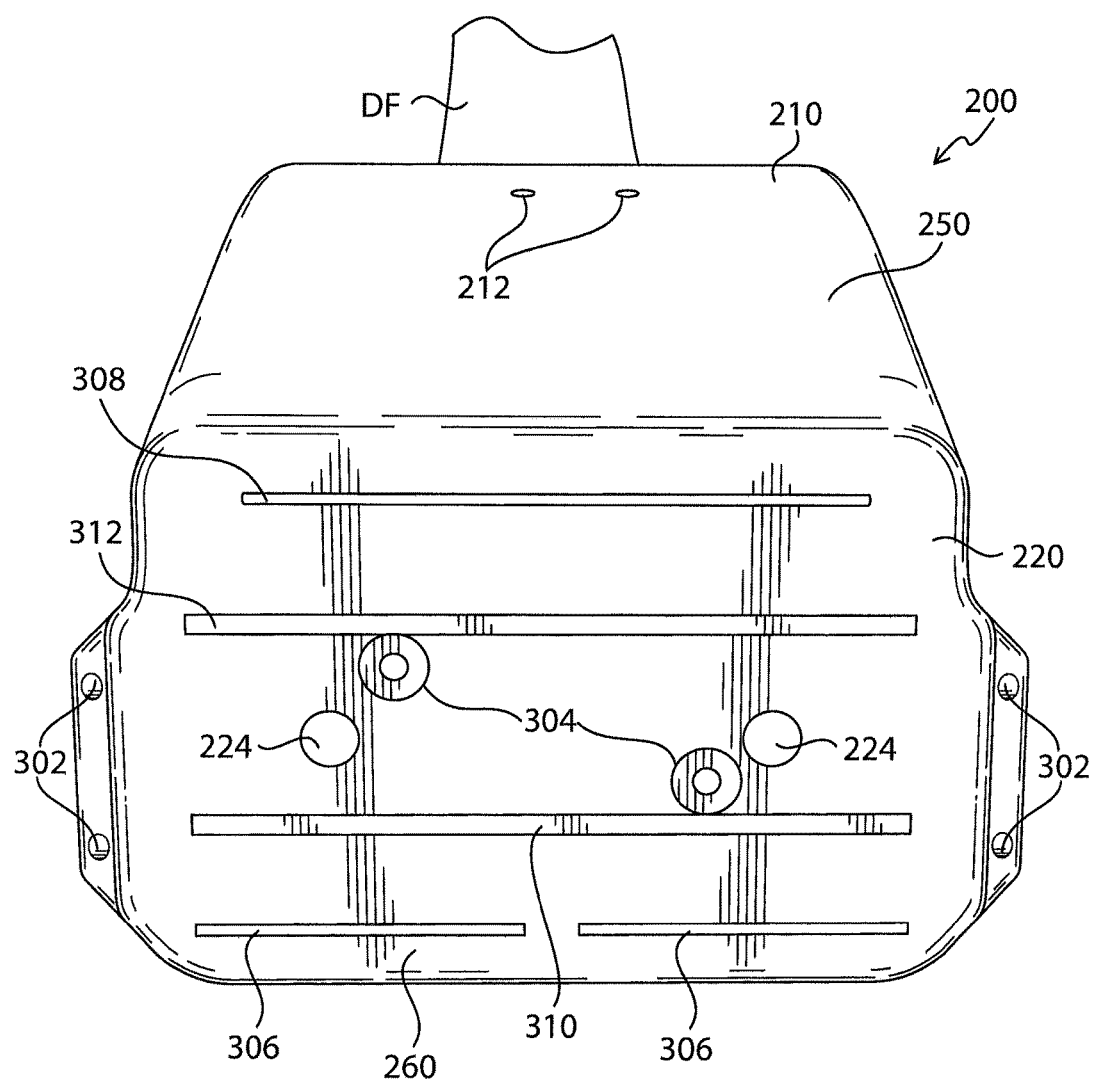
FIG. 25 shows a bottom perspective view of a distal femur cutting block according to at least one embodiment of the present disclosure in the presence of a distal femur.

FIG. 25 shows a bottom perspective view of a distal femur cutting block 200 according to at least one embodiment of the present disclosure closed around a distal femur. After distal femur cutting block 200 is closed around a distal femur, pins or screws may be inserted through pin guides 302 and 304 into the patient's distal femur in order to securely mount distal femur cutting block 200 to the patient's distal femur for a knee implant surgical procedure. As discussed herein, after distal femur cutting block 200 is positioned around a patient's distal femur and after distal femur cutting block 200 is secured to a patient's distal femur by pins or screws inserted through pin guides 212, 302, and 304 into the patient's distal femur, cutting instruments may be inserted through cutting guides 224, 306, 308, 310, and 312 in order to accurately cut the femoral condyles into the shape needed to receive a knee implant or to accurately drill holes into the femoral condyles to facilitate attachment of a knee implant. Such cuts may include one or more of posterior cut, posterior chamber cut, anterior chamber cut, anterior cut, distal femoral cut, and transition cut.

Figure 26:
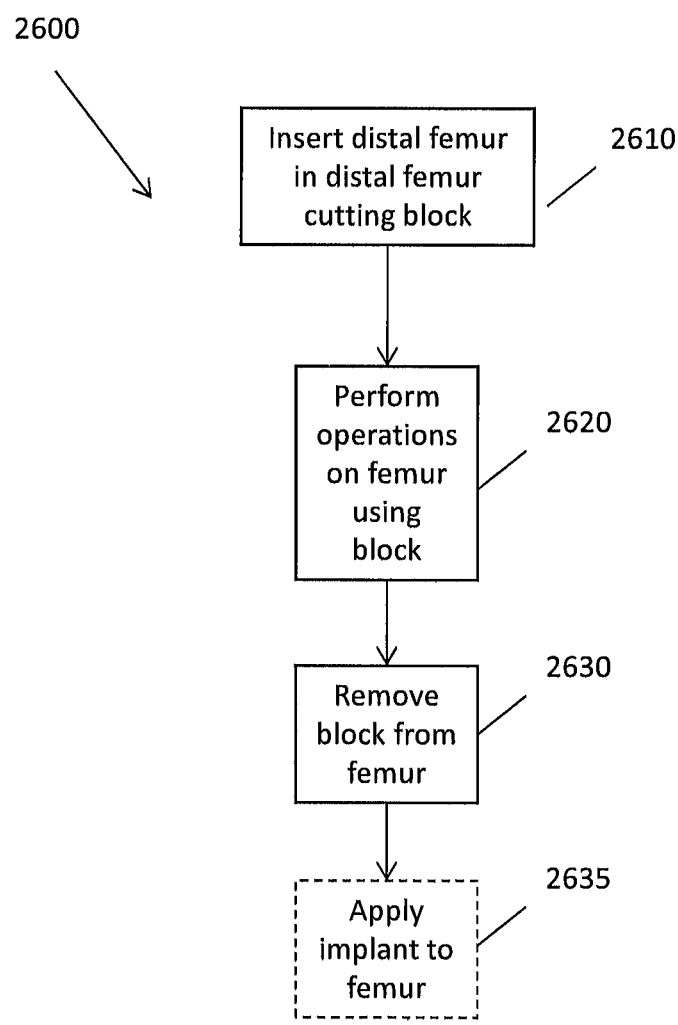
FIG. 26 shows a flowchart illustrating a method of utilizing a distal femur cutting block according to at least one embodiment of the present disclosure.

FIG. 26 shows a method 2600 of utilizing a distal femur cutting block according to at least one embodiment of the present disclosure. As shown in FIG. 26, such a method includes the step 2610 of applying the distal femur cutting block to the patient's distal femur. In particular, the distal femur cutting block may be arranged into an open configuration (as described herein) such that the distal femur can be received by the distal femur cutting block. After at least a portion of the distal femur is received by the distal femur cutting block, the block is adjusted to be in a closed configuration (as described herein) in order to closely mate with the distal femur and substantially lock the block in place relative to the distal femur. As shown in FIG. 26, the method 2600 also includes the step 2620 of performing procedures on the distal femur using the guides on the surfaces of the block, such as, for example, pinning down the block anteriorly and/or distally to the distal femur and carrying out a series of cuts to the distal femur including one or more of posterior cut, posterior chamber cut, anterior chamber cut, anterior cut, distal femoral cut, and transition cut. As shown in FIG. 26, the method 2600 also includes the step 2630 of taking the block off of the distal femur. This step 2630 may include removing one or more pins that were applied in step 2620. FIG. 26 also shows that the method 2600 may optionally include the step 2635 of applying an implant to the distal femur.

FIGS. 27-32 show sides view of a distal femur cutting block 1100 illustrating its use cutting instruments. As shown in FIGS. 27-32, distal femur cutting block 1100 is attached to distal femur by pins 303 inserted through pin guides 302, and also by pins inserted through other pin guides not shown in FIGS. 27-32.

Figure 27:
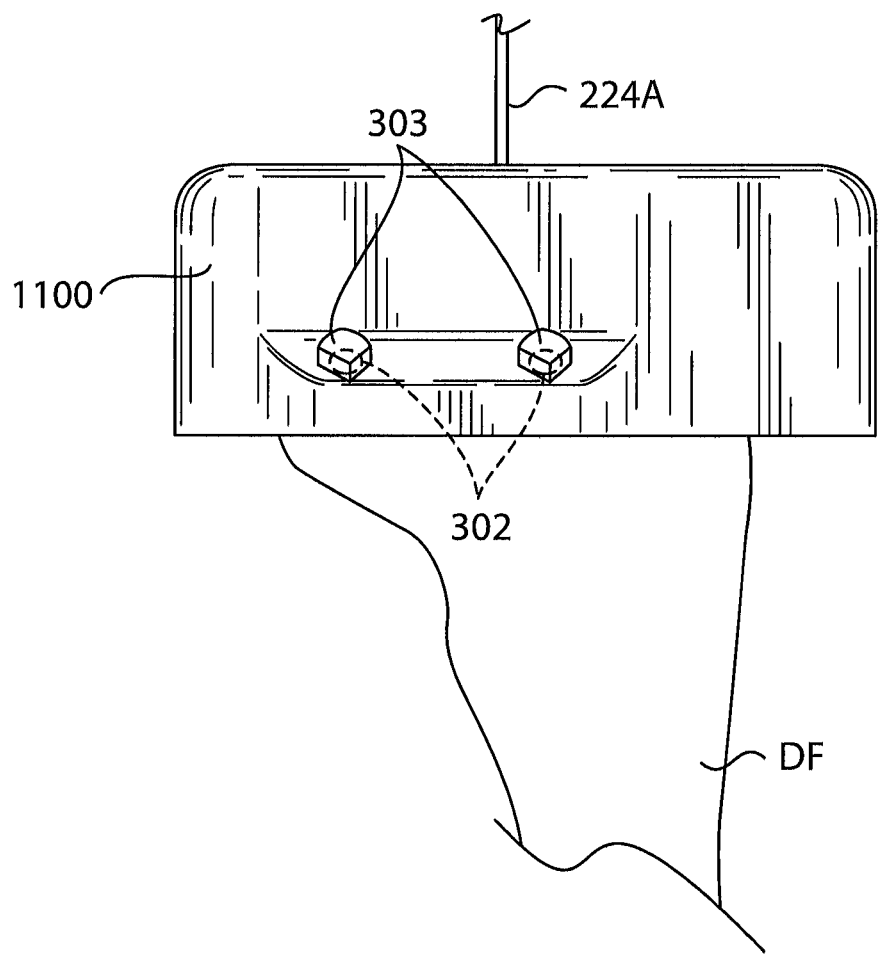
FIG. 27 shows a side view of a distal femur cutting block according to at least one embodiment of the present disclosure in the presence of a distal femur.
Figure 28:
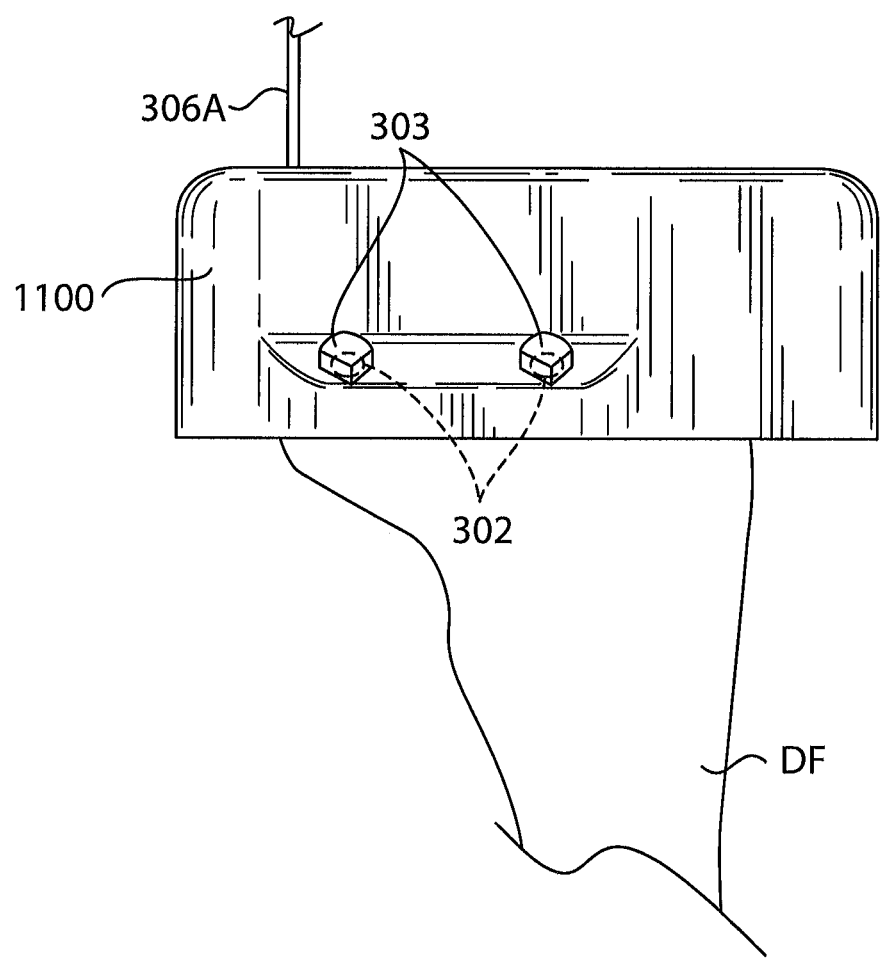
FIG. 28 shows a side view of a distal femur cutting block according to at least one embodiment of the present disclosure in the presence of a distal femur.
Figure 29:
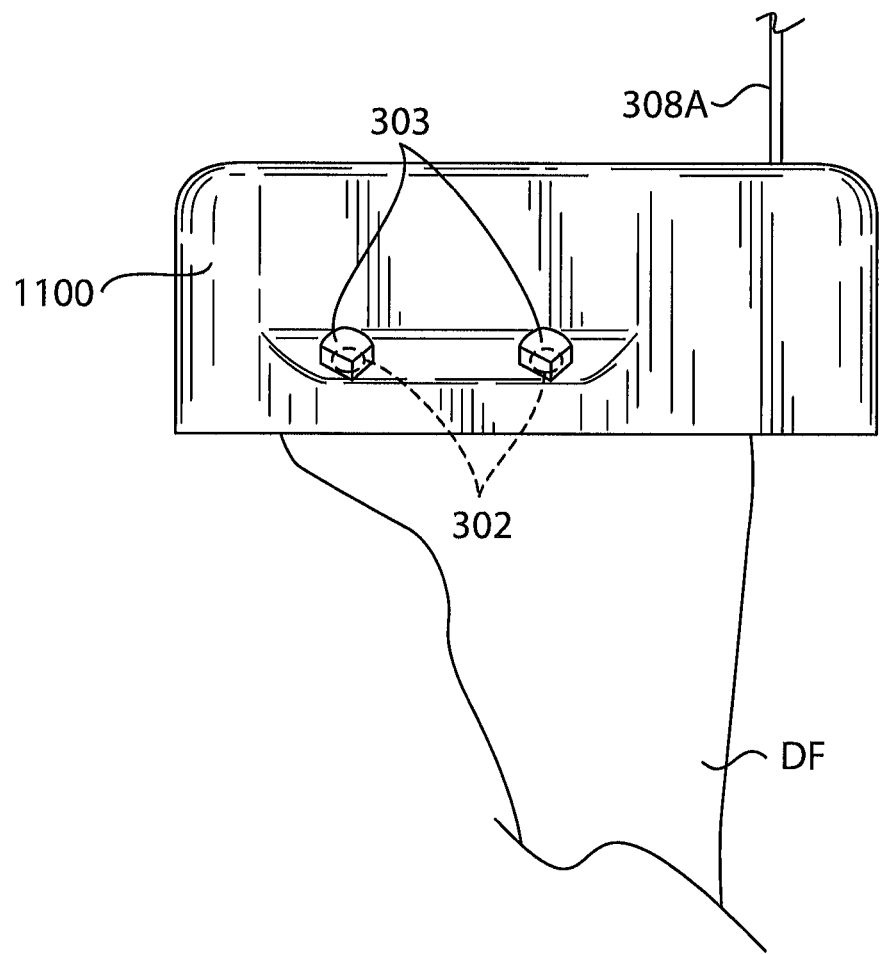
FIG. 29 shows a side view of a distal femur cutting block according to at least one embodiment of the present disclosure in the presence of a distal femur.
Figure 30:
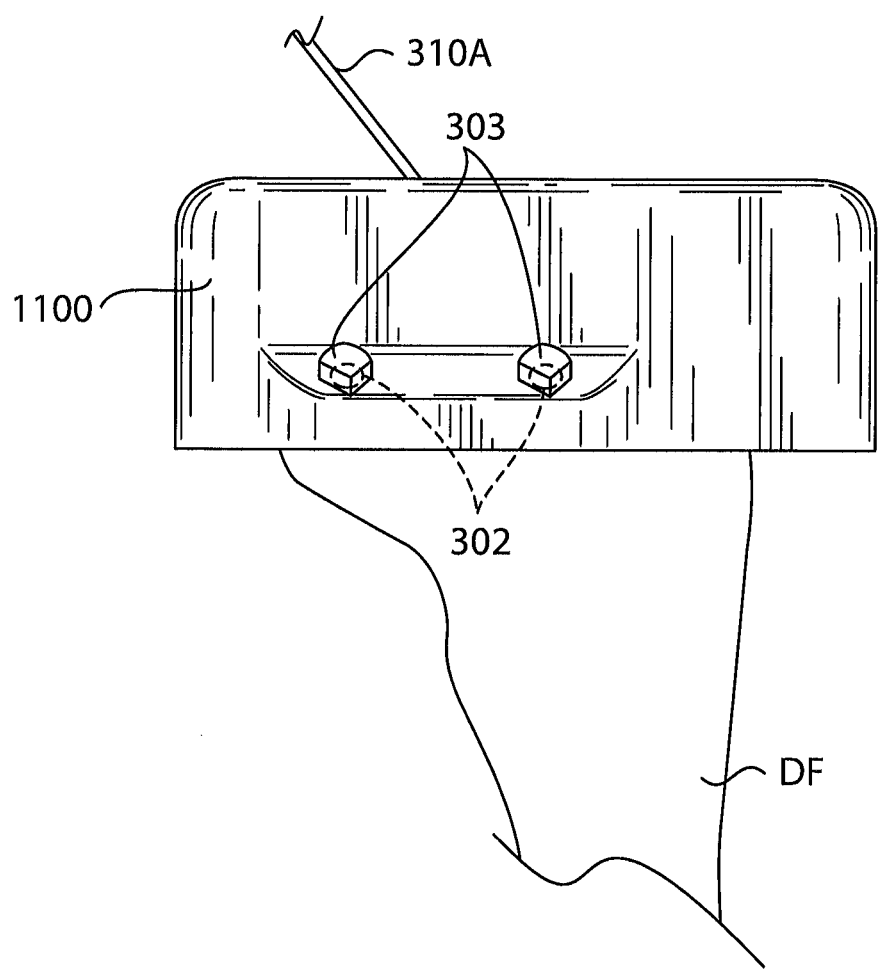
FIG. 30 shows a side view of a distal femur cutting block according to at least one embodiment of the present disclosure in the presence of a distal femur.
Figure 31:
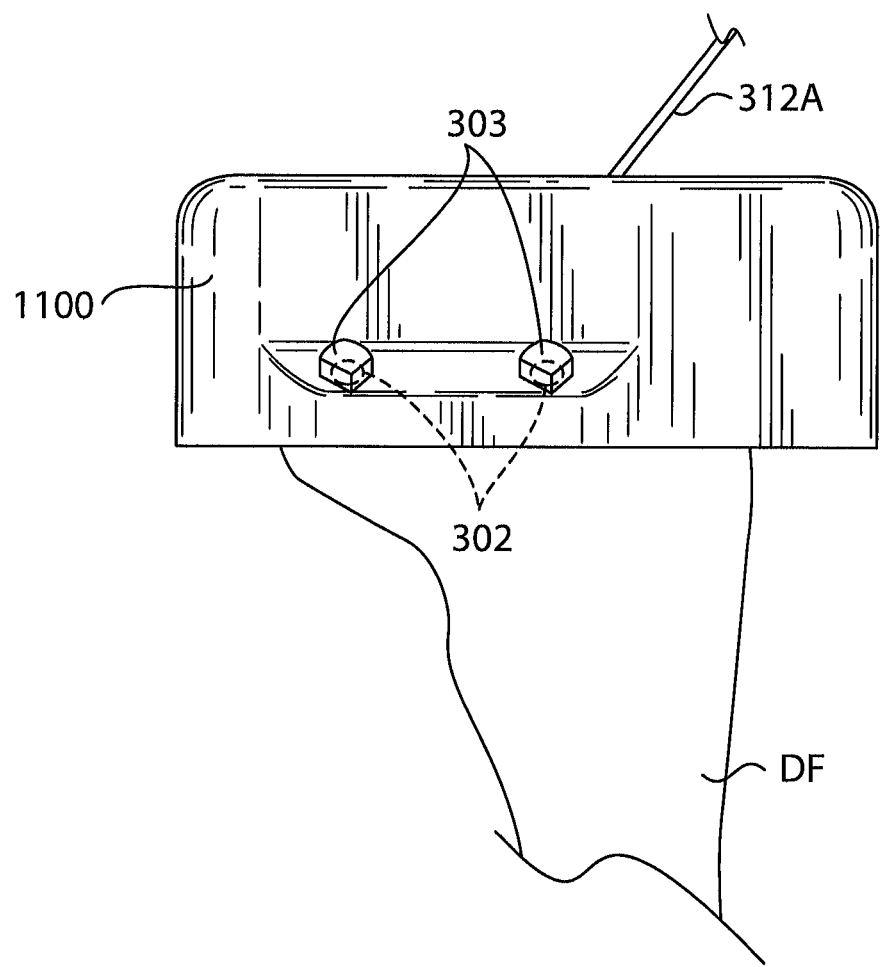
FIG. 31 shows a side view of a distal femur cutting block according to at least one embodiment of the present disclosure in the presence of a distal femur.
Figure 32:
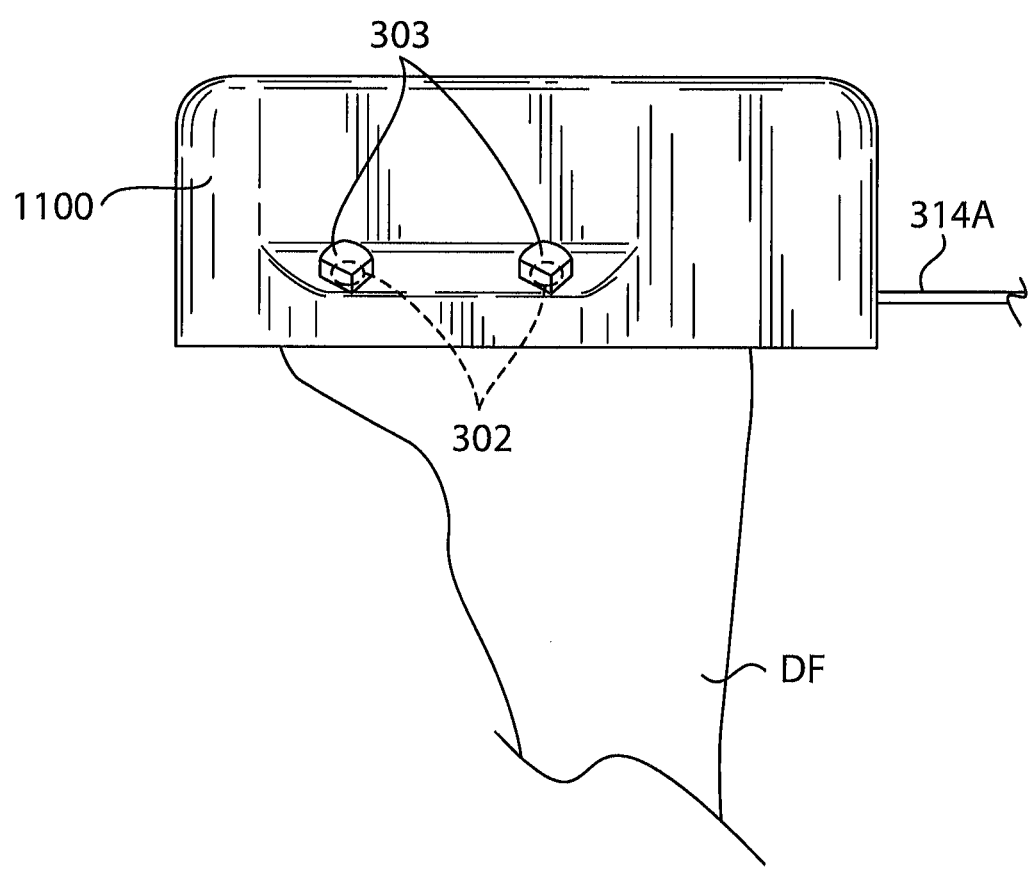
FIG. 32 shows a side view of a distal femur cutting block according to at least one embodiment of the present disclosure in the presence of a distal femur.

In FIG. 27, cutting tool 224A is inserted into cutting guide 224. Cutting tool 224A in this example is a drill. In FIG. 28, cutting tool 306A is inserted into cutting guide 306. Cutting tool 306A in this example is a saw. In FIG. 29, cutting tool 308A is inserted into cutting guide 308. Cutting tool 308A in this example is a saw. In FIG. 30, cutting tool 310A is inserted into cutting guide 310. Cutting tool 310A in this example is a saw. In FIG. 31, cutting tool 312A is inserted into cutting guide 312. Cutting tool 312A in this example is a saw. In FIG. 32, cutting tool 314A is inserted into cutting guide 314. Cutting tool 314A in this example is a saw.

Figure 33:
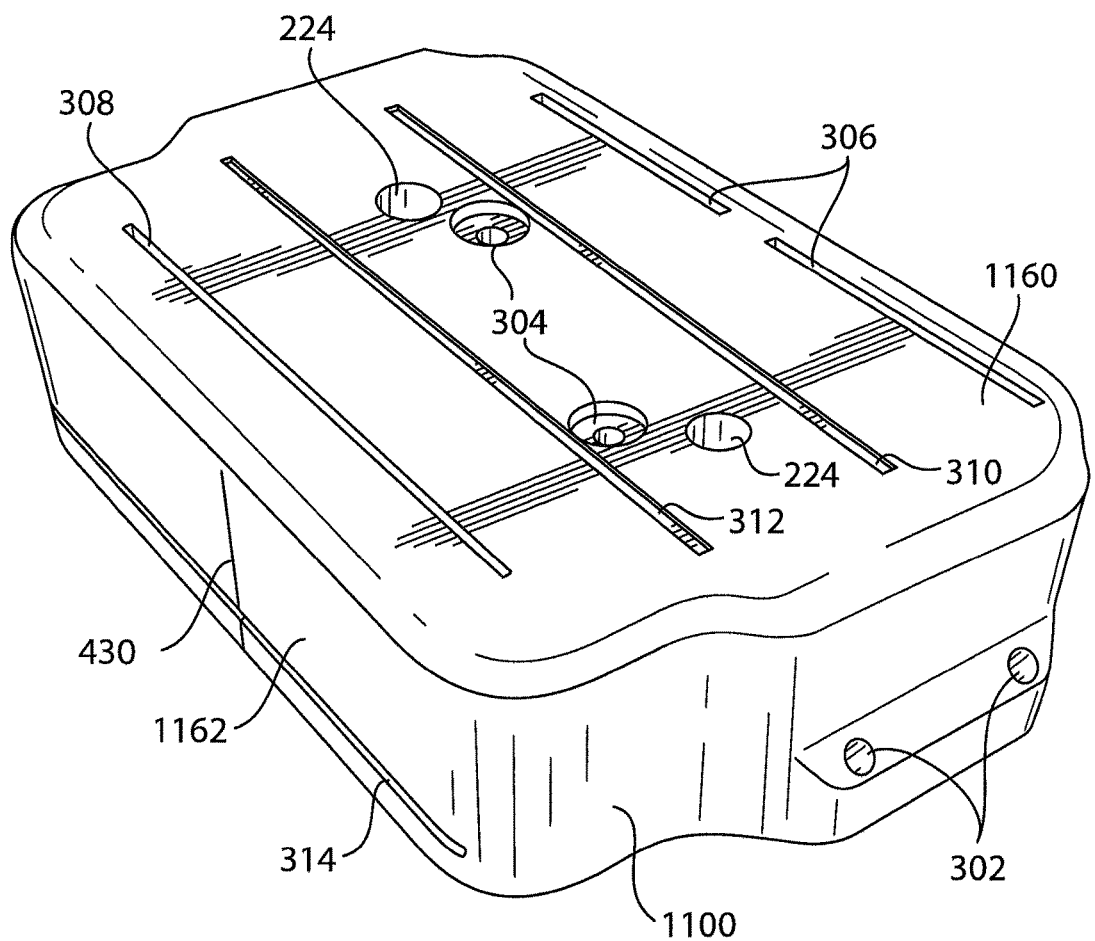
FIG. 33 shows a bottom perspective view of a distal femur cutting block according to at least one embodiment of the present disclosure.

FIG. 33 shows a bottom perspective view of a distal femur cutting block 1100 according to at least one embodiment of the present disclosure. As discussed elsewhere herein, distal femur cutting block 1100 according to the present disclosure may be formed of a variety of suitable materials, including, but not limited to, nylon. Shown in FIG. 33 are pin guides 302 and 304. Pin guides 302 and 304 extend completely through distal femur cutting block 1100. In at least one embodiment, one or more of pin guides 302 and 304 may comprise a countersink configuration. Also shown in FIG. 33 is hinge 430, which is formed in distal femur cutting block 1100 at approximately the midpoint of front surface 1162. Although hinge 430 is shown in FIG. 33 at approximately the midpoint of front surface 1162, the location of hinge 430 is not limited to this position. Hinge 430 may be offset toward one end of distal femur cutting block 1100 or the other. Hinge 430 may be formed across the longer dimension of distal femur cutting block 1100 (i.e., perpendicular to the orientation shown in FIG. 33), at or near the midpoint or offset toward one end of distal femur cutting block 1100 or the other. Hinge 430 also may be formed at a diagonal between opposing surfaces of distal femur cutting block 1100. When distal femur cutting block 1100 is positioned on a patient's distal femur, pins or screws may be inserted through pin guides 302 and 304 into the patient's distal femur in order to securely mount distal femur cutting block 1100 to the patient's distal femur for a knee implant surgical procedure. Also shown in FIG. 33 are cutting guides 224, 306, 308, 310, 312, and 314. Cutting guides 224, 306, 308, 310, 312, and 314 extend through distal femur cutting block 1100. In at least one embodiment, one or more of cutting guides 224, 306, and 308 may extend through distal femur cutting block 1100 in an alignment that is substantially perpendicular to bottom surface 1160 of distal femur cutting block 1100. In at least one embodiment, one or more of cutting guides 310 and 312 may extend through distal femur cutting block 1100 in an alignment that is not perpendicular to the bottom surface 1160 of distal femur cutting block 1100. In at least one embodiment, cutting guide 314 may extend through distal femur cutting block 1100 in an alignment that is substantially perpendicular to front surface 1162 of distal femur cutting block 1100. As discussed herein, distal femur cutting block 1100 can be flexed at hinge 430 in order to position on distal femur cutting block 1100 on a patient's distal femur. Distal femur cutting block 1100 then can be secured to the patient's distal femur, and cutting instruments may be inserted thorough cutting guides 224, 306, 308, 310, 312, and 314 in order to accurately cut the femoral condyles into the shape needed to receive a knee implant, or to accurately drill holes into the femoral condyles to facilitate attachment of a knee implant. The placement of pin guides 302 and 304, and cutting guides 224, 306, 308, 310, 312, and 314 may be determined through the use of CT scans and/or MRI scans in order to ensure that once distal femur cutting block 1100 is attached to the distal femur, the surgeon or other medical professional will have the correct locations to cut the femoral condyles and/or insert pins. By having all of the cuts performed with the guidance of a single distal femur cutting block 1100 (instead of multiple blocks used sequentially to carry out the needed cuts), the errors associated with cutting the distal femur can be reduced and patient outcomes can be improved.

Figure 34:
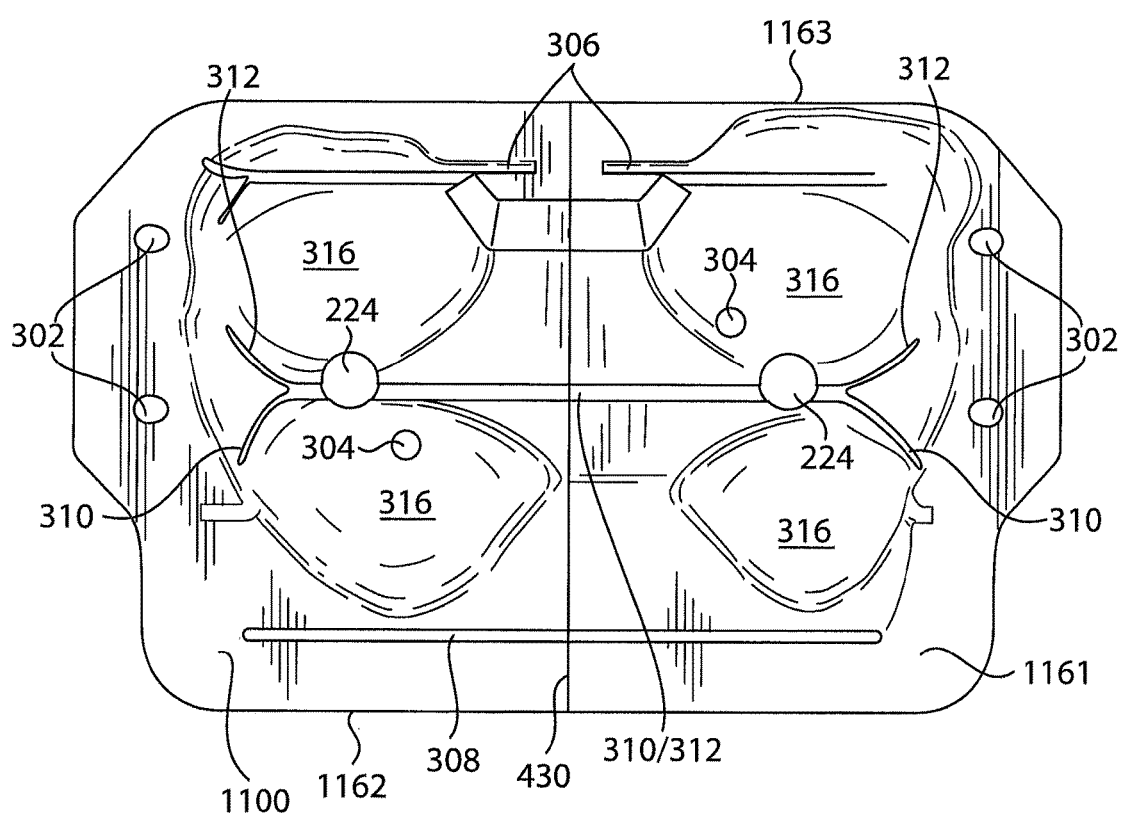
FIG. 34 shows a top view of a distal femur cutting block according to at least one embodiment of the present disclosure.

FIG. 34 shows a top view of a distal femur cutting block 1100 according to at least one embodiment of the present disclosure, including top surface 1161, front surface 1162, and rear surface 1163. Shown in FIG. 34 are pin guides 302 and 304, and cutting guides 224, 306, 308, 310, and 312. Also shown in FIG. 34 are impressions 316. Impressions 316 comprise contoured portions of the top surface 1161 of distal femur cutting block 1100. Impressions 316 are contoured to fit against the femoral condyles. Through the use of CT scans and/or MRIs, the contours of impressions 316 may be configured to closely match at least a portion of the femoral condyles. Also shown in FIG. 34 is the location of hinge 430, which is formed in distal femur cutting block 1100 at approximately the midpoint of top surface 1161. Although hinge 430 is shown in FIG. 34 at approximately the midpoint of top surface 1161, the location of hinge 430 is not limited to this position. Hinge 430 may be offset toward one end of distal femur cutting block 1100 or the other. Hinge 430 may be formed across the longer dimension of distal femur cutting block 1100 (i.e., perpendicular to the orientation shown in FIG. 34), at or near the midpoint or offset toward one end of distal femur cutting block 1100 or the other. Hinge 430 also may be formed at a diagonal between opposing surfaces of distal femur cutting block 1100. As discussed herein, distal femur cutting block 1100 can be flexed at hinge 430, thereby separating top surface 1161 in order to facilitate positioning of distal femur cutting block 1100 on a patient's distal femur.

Figure 35:
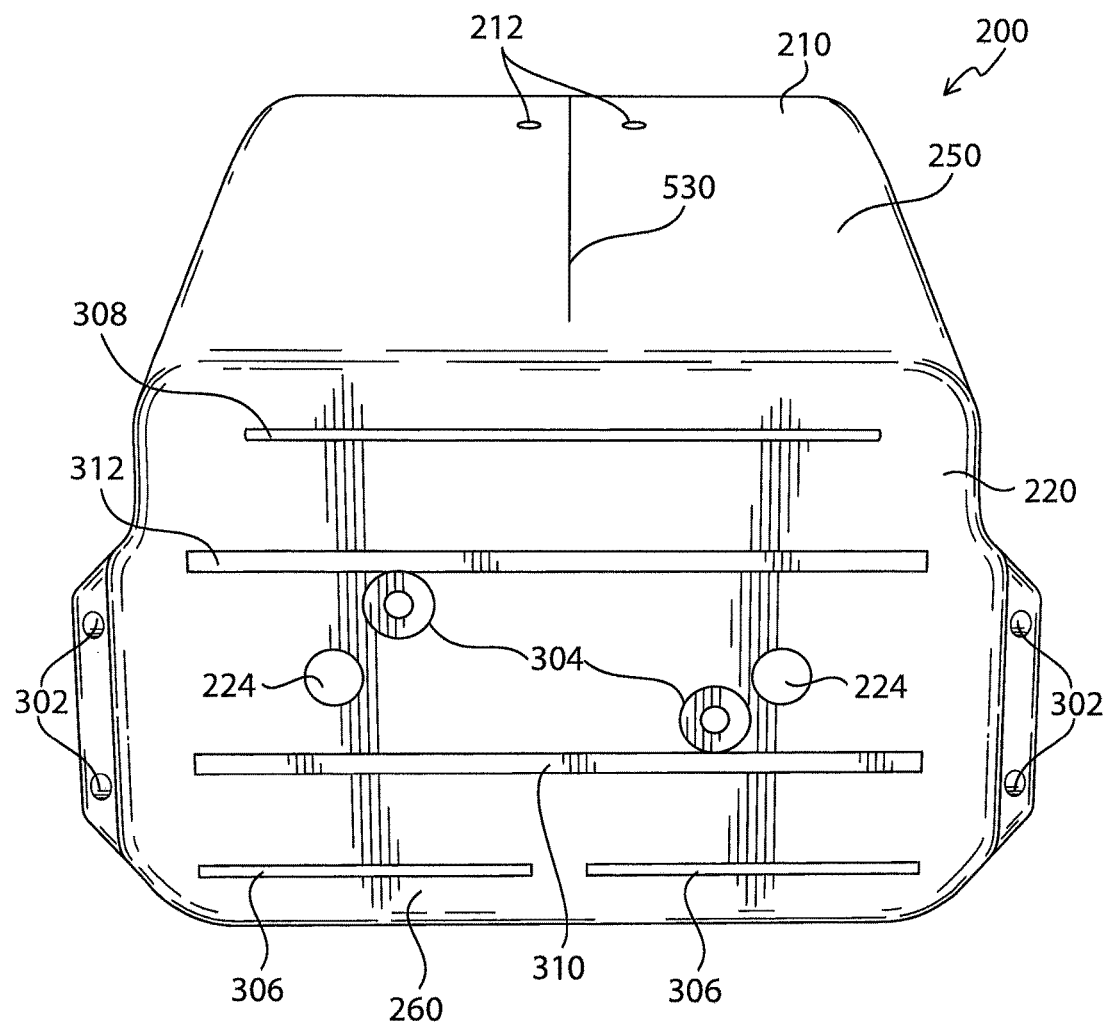
FIG. 35 shows a bottom perspective view of a distal femur cutting block according to at least one embodiment of the present disclosure.

FIG. 35 shows a bottom perspective view of a distal femur cutting block 200 according to at least one embodiment of the present disclosure. FIG. 35 shows anterior portion 210 including anterior surface 250, and distal portion 220 including distal surface 260. Shown in FIG. 35 are pin guides 212, 302, and 304. Pin guides 212 extend completely through anterior portion 210. Pin guides 302 and 304 extend completely through distal portion 220. In at least one embodiment, one or more of pin guides 212, 302, and 304 may comprise a countersink configuration. Also shown in FIG. 35 is the location of hinge 530, which is formed in distal femur cutting block 200 at approximately the midpoint of distal portion 220. Although hinge 530 is shown in FIG. 35 at approximately the midpoint of distal portion 220, the location of hinge 530 is not limited to this position. Hinge 530 may be offset toward one end of distal femur cutting block 200 or the other. Hinge 530 also may be formed at a diagonal. As discussed herein, distal femur cutting block 200 can be flexed at hinge 530, thereby separating anterior portion 210 in order to facilitate positioning of distal femur cutting block 200 on a patient's distal femur. As discussed herein, when distal femur cutting block 200 is positioned around a patient's distal femur, pins or screws may be inserted through pin guides 212, 302, and 304 into the patient's distal femur in order to securely mount distal femur cutting block 200 to the patient's distal femur for a knee implant surgical procedure. Also shown in FIG. 35 are cutting guides 224, 306, 308, 310, and 312. Cutting guides 224, 306, 308, 310, and 312 extend through distal portion 220. In at least one embodiment, cutting guides 224, 306, and 308 may extend through distal portion 220 in an alignment that is substantially perpendicular to the bottom surface of distal portion 220. In at least one embodiment, a cutting guides 310 and 312 may extend through distal portion 220 in an alignment that is not perpendicular to the bottom surface of distal portion 220. As discussed herein, after distal femur cutting block 200 is positioned around and secured to a patient's distal femur, cutting instruments may be inserted thorough cutting guides 224, 306, 308, 310, and 312 in order to accurately cut the femoral condyles into the shape needed to receive a knee implant, or to accurately drill holes into the femoral condyles to facilitate attachment of a knee implant. The placement of pin guides 212, 302, and 304, and cutting guides 224, 306, 308, 310, and 312 may be determined through the use of CT scans and/or MRI scans in order to ensure that once the block 200 is attached to the distal femur, the surgeon or other medical professional will have the correct locations to cut the femoral condyles and/or insert pins.

Figure 36:
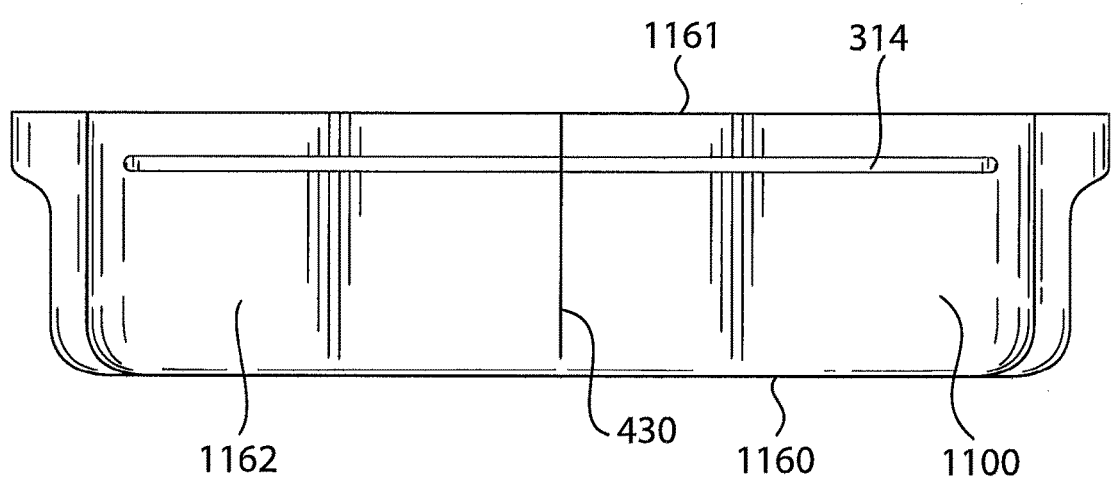
FIG. 36 shows an anterior view of a distal femur cutting block according to at least one embodiment of the present disclosure.

FIG. 36 shows an anterior view of a distal femur cutting block 1100 according to at least one embodiment of the present disclosure. Shown in FIG. 36 is front surface 1162 with cutting guide 314 extending therethrough. Also shown in FIG. 36 is hinge 430, which is formed in distal femur cutting block 1100 at approximately the midpoint of front surface 1162. As discussed herein, distal femur cutting block 1100 can be flexed at hinge 430 in order to position on distal femur cutting block 1100 on a patient's distal femur. Distal femur cutting block 1100 then can be secured to the patient's distal femur, and cutting instruments may be inserted through the cutting guide in order to accurately cut the femoral condyles into the shape needed to receive a knee implant, or to accurately drill holes into the femoral condyles to facilitate attachment of a knee implant. The placement of cutting guide 314 may be determined through the use of CT scans and/or MRI scans in order to ensure that once distal femur cutting block 1100 is attached to the distal femur, the surgeon or other medical professional will have the correct locations to cut the femoral condyles and/or insert pins.

Figure 37:
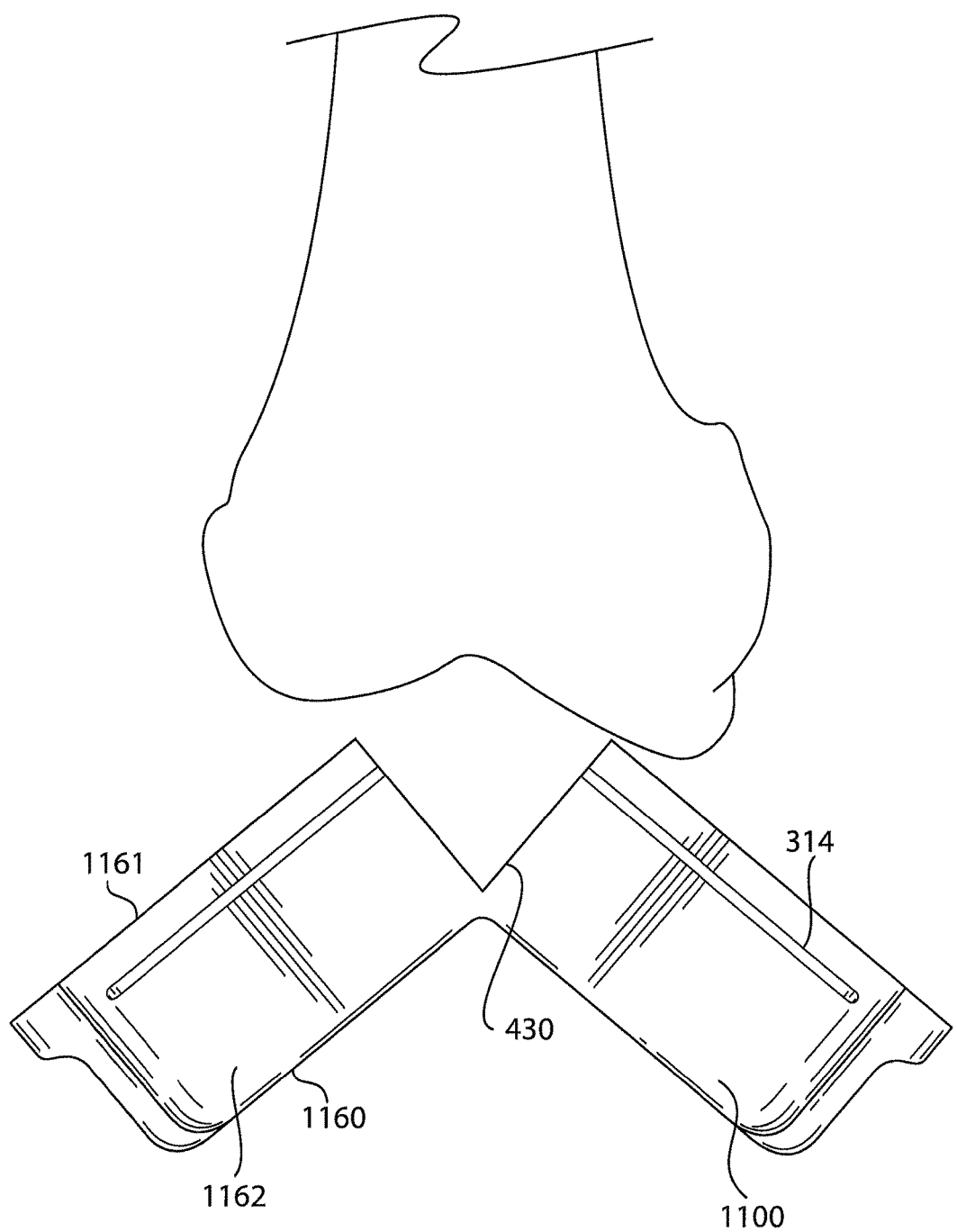
FIG. 37 shows an anterior view of a distal femur cutting block according to at least one embodiment of the present disclosure in the presence of a distal femur.
Figure 38:
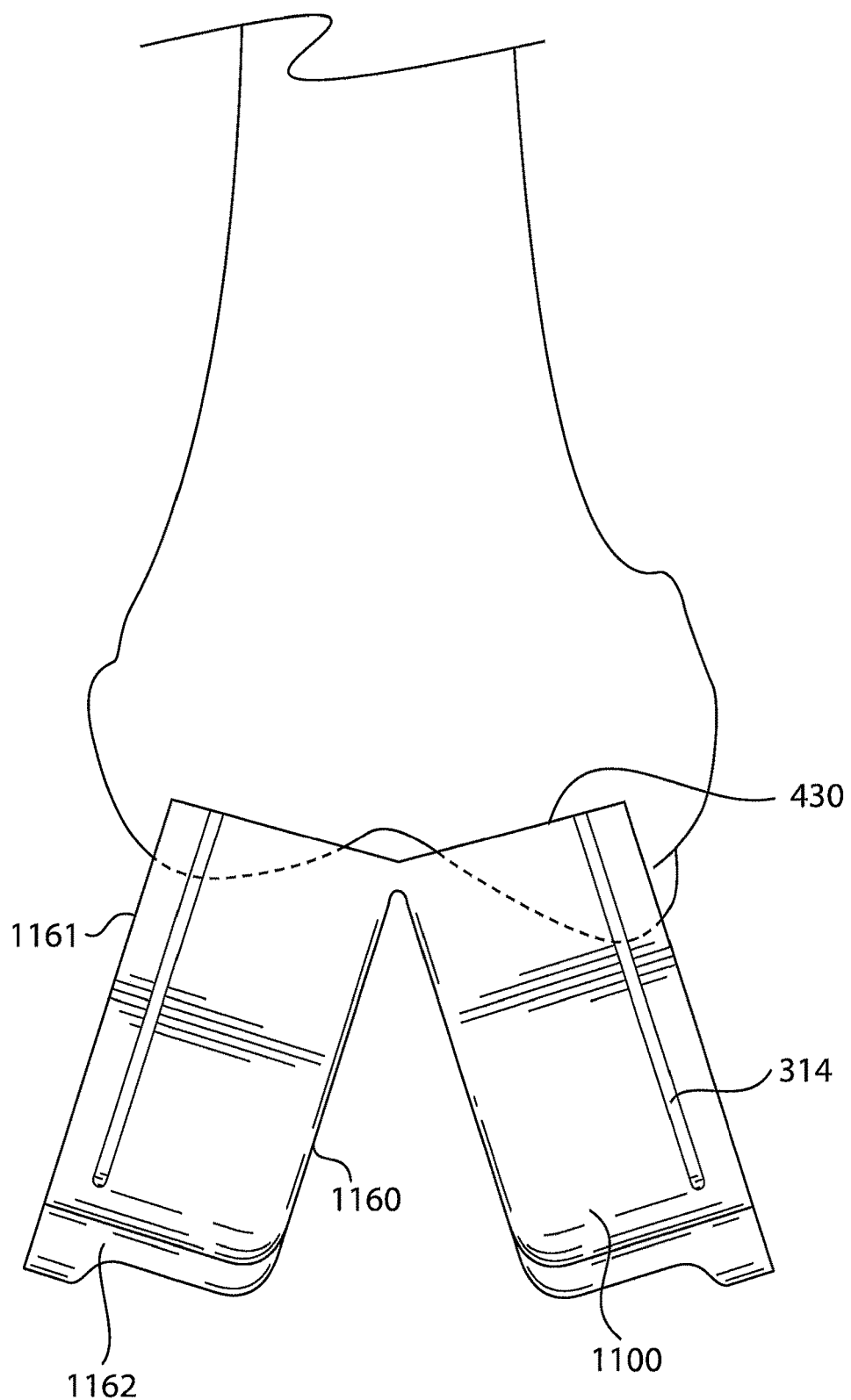
FIG. 38 shows an anterior view of a distal femur cutting block according to at least one embodiment of the present disclosure in the presence of a distal femur.
Figure 39:
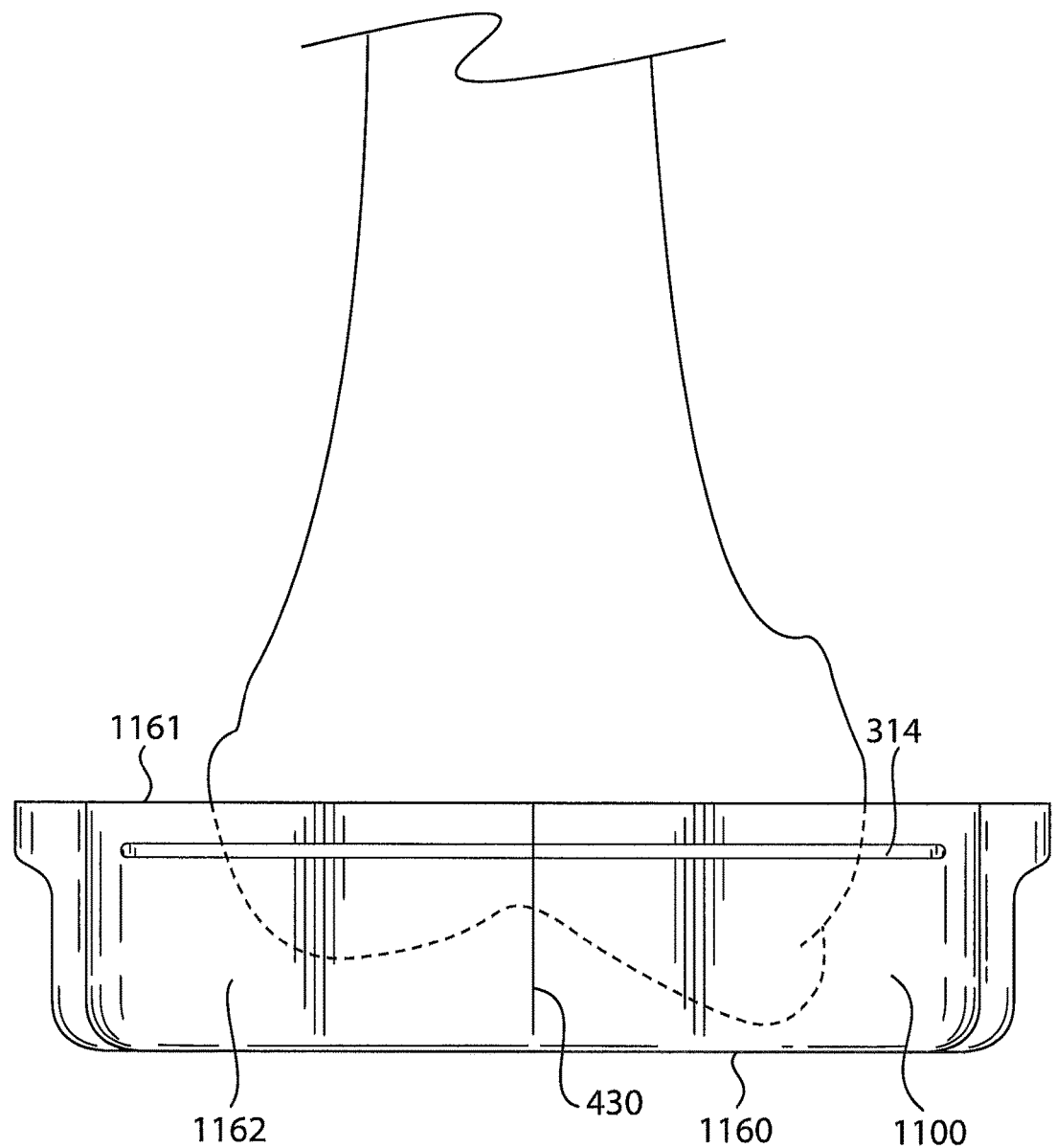
FIG. 39 shows an anterior view of a distal femur cutting block according to at least one embodiment of the present disclosure in the presence of a distal femur.

FIGS. 37-39 show a step-by-step process of applying distal femur cutting block 1100 to a distal femur DF, according to at least one embodiment of the present disclosure. As shown in FIG. 37, distal femur cutting block 1100 is flexed at hinge 430 to form an open configuration such that the distal femur DF can be received within distal femur cutting block 1100. As shown in FIG. 38, distal femur DF is inserted within the distal femur cutting block 1100, which is still in the flexed configuration. As shown in FIG. 39, distal femur cutting block 1100 is flexed back around hinge 430 and distal femur cutting block 1100 is closed around distal femur DF. As shown in FIG. 39, hinge 430 is in a closed position and distal femur cutting block 1100 is closed around distal femur DF. Distal femur cutting block 1100 then can be secured to distal femur DF.

While this disclosure has been described as having various embodiments, these embodiments according to the present disclosure can be further modified within the scope and spirit of this disclosure. This application is therefore intended to cover any variations, uses, or adaptations of the disclosure using its general principles. For example, any methods disclosed herein represent one possible sequence of performing the steps thereof. A practitioner may determine in a particular implementation that a plurality of steps of one or more of the disclosed methods may be combinable, or that a different sequence of steps may be employed to accomplish the same results. Each such implementation falls within the scope of the present disclosure as disclosed herein and in the appended claims. Furthermore, this application is intended to cover such departures from the present disclosure as come within known or customary practice in the art to which this disclosure pertains.

I claim:

1. A distal femur cutting block comprising:
   a first portion defining a first external surface, said first external surface including one or more first passages therethrough;
   a second portion defining a second external surface, said second external surface including one or more second passages therethrough, said first portion formed integral with and hingedly connected to said second portion along a seam separating said first and second portions, wherein said first portion and said second portion may be rotated relative to each other through said hinged connection;
   a third internal surface opposite one of said first external surface or said second external surface, said third internal surface comprising contours configured to substantially mate with at least one condyle of said distal femur; and
   a fourth internal surface opposite said other one of said first external surface or said second external surface, said fourth internal surface comprising contours configured to substantially mate with said at least one condyle of said distal femur.

2. The distal femur cutting block of claim 1, wherein at least one of said one or more first passages comprises a cylindrical passage sized to receive a pin for fastening said first portion to said distal femur.

3. The distal femur cutting block of claim 1, wherein at least one of said one or more second passages comprises a cylindrical passage sized to receive a drill for removing bone from said distal femur.

4. The distal femur cutting block of claim 1, wherein at least one of said one or more second passages comprises a slot sized to receive an orthopedic bone saw blade for cutting said distal femur.

5. The distal femur cutting block of claim 1, wherein said one or more second passages comprise slots for receiving one or more orthopedic bone saw blades, said slots being sufficient in number and arrangement to enable said distal femur in contact with said third internal surface to be shaped for receiving a femoral implant without removing said distal femur from said distal femur cutting block.

6. The distal femur cutting block of claim 1, wherein said first portion, said second portion, and said hinged connection are constructed from a single nylon article.

7. A distal femur cutting block comprising:
- a first portion defining a first external surface, said first external surface containing one or more first passages therethrough, said first portion comprising a seam along a longitudinal axis thereof, said seam dividing said first portion into two substantially similar sections;
- a second portion defining a second external surface, said second external surface containing one or more second passages therethrough, said second portion being integral with and arranged at substantially a right angle to said first portion, said seam continuing into said second portion but not through said second external surface thereby forming a hinge at said second external surface; and
- a third surface opposite one of said first surface or said second surface, said third surface comprising contours configured to substantially mate with at least one condyle of said distal femur.

8. The distal femur cutting block of claim 7, wherein at least one of said one or more first passages comprises a cylindrical passage sized to receive a pin for fastening said first portion to said distal femur.

9. The distal femur cutting block of claim 7, wherein at least one of said one or more second passages comprises a cylindrical passage sized to receive a drill for removing bone from said distal femur.

10. The distal femur cutting block of claim 7, wherein at least one of said one or more second passages comprises a slot sized to receive an orthopedic bone saw blade for cutting said distal femur.

11. The distal femur cutting block of claim 7, wherein said one or more second passages comprise slots for receiving one or more orthopedic bone saw blades, said slots being sufficient in number and arrangement to enable said distal femur in contact with said third surface to be shaped for receiving a femoral implant without removing said distal femur from said distal femur cutting block.

12. The distal femur cutting block of claim 7, wherein said first portion and said second portion are constructed from a single nylon article.

13. A distal femur cutting block comprising:
- a block having a first surface, said first surface comprising contours configured to substantially mate with at least one condyle of a distal femur, and a second surface opposing said first surface;
- at least one passage through said block, said at least one passage configured to permit a medical instrument introduced into said passage at said first surface to emerge from said passage at said second surface, wherein when said second surface is adjacent said at least one condyle of said distal femur, said medical instrument is aligned by said passage into a position to contact said at least one condyle; and
- a seam along said first surface, said seam dividing said first surface into two substantially similar sections, said seam continuing into said block but not through said second surface thereby forming a hinge at said second surface.

14. The distal femur cutting block of claim 13, wherein said at least one passage comprises a cylindrical passage sized to receive a pin for fastening said block to said distal femur.

15. The distal femur cutting block of claim 13, wherein said at least one passage comprises a cylindrical passage sized to receive a drill for removing bone from said distal femur.

16. The distal femur cutting block of claim 13, wherein said at least one passage comprises a slot sized to receive an orthopedic bone saw blade for cutting said distal femur.

17. The distal femur cutting block of claim 13, comprising a plurality of passages, wherein said passages comprise slots for receiving one or more orthopedic bone saw blades, said slots being sufficient in number and arrangement to enable said distal femur in contact with said first surface to be shaped for receiving a femoral implant without removing said distal femur from said contact with said first surface.

* * * * *